United States Patent
Becken et al.

(10) Patent No.: US 8,506,076 B2
(45) Date of Patent: Aug. 13, 2013

(54) OPTIMIZATION AND PRODUCTION OF AN EYEGLASS LENS FOR CORRECTING AN ASTIGMATIC REFRACTION

(75) Inventors: Wolfgang Becken, Munich (DE); Andrea Welk, Munich (DE); Anne Seidemann, Munich (DE); Gregor Esser, Munich (DE); Helmut Altheimer, Baisweil-Lauchdorf (DE); Dietmar Uttenweiler, Icking (DE)

(73) Assignee: Rodenstock GmbH, Munich (DE)

( * ) Notice: Subject to any disclaimer, the term of this patent is extended or adjusted under 35 U.S.C. 154(b) by 211 days.

(21) Appl. No.: 13/129,354

(22) PCT Filed: Nov. 12, 2009

(86) PCT No.: PCT/EP2009/008069
§ 371 (c)(1),
(2), (4) Date: Aug. 3, 2011

(87) PCT Pub. No.: WO2010/054817
PCT Pub. Date: May 20, 2010

(65) Prior Publication Data
US 2011/0299032 A1     Dec. 8, 2011

(30) Foreign Application Priority Data
Nov. 13, 2008 (DE) .......................... 10 2008 057 205
Nov. 13, 2008 (DE) .......................... 10 2008 057 206

(51) Int. Cl.
*G02C 7/02* (2006.01)
*A61B 3/14* (2006.01)
*A61B 3/113* (2006.01)

(52) U.S. Cl.
CPC *G02C 7/025* (2013.01); *A61B 3/113* (2013.01)
USPC .................. 351/159.73; 351/159.77; 351/209

(58) Field of Classification Search
CPC ................................. G02C 7/025; A61B 3/113
USPC .............. 351/159.73–159.78, 205, 209, 212, 351/246, 247; 33/200; 702/19
See application file for complete search history.

(56) References Cited

U.S. PATENT DOCUMENTS
4,613,217 A    9/1986  Fuerter et al.
6,382,789 B1   5/2002  Baudart et al.
(Continued)

FOREIGN PATENT DOCUMENTS
EP   0 039 498 A2   11/1981
EP   1 837 699 A1    9/2007
(Continued)

*Primary Examiner* — Huy K Mai
(74) *Attorney, Agent, or Firm* — Schiff Hardin LLP

(57) ABSTRACT

A method and system for producing a first spectacle lens for a specific situation of wear for correcting at least a first astigmatic refraction of a first eye of a wearer, which has a first cylinder reference axis $\alpha_0^{(1)}$ in a reference direction of sight $-e_z^{(1)}$ of the first eye. According to the method and apparatus, a primary direction of sight $-e_\zeta^{(1,p)}$ of the first eye for at least one primary evaluation point $i_b^{(1,p)}$ of the first spectacle lens is determined and a corresponding primary direction of sight $-e_{\zeta,k}^{(2,p)}$ of a second eye of the spectacle wearer that corresponds to the primary direction of sight $-e_\zeta^{(1,p)}$ of the first eye in the specific situation of wear is also determined. Furthermore, a first primary merit function for at least one surface of the first spectacle lens is minimized, in which the first primary merit function for the at least one primary evaluation point $i_b^{(1,p)}$ of the first spectacle lens takes into account a correction of a first primary transformed astigmatic refraction by the first spectacle lens in the specific situation of wear such that the first primary transformed astigmatic refraction depends on the corresponding primary direction of sight $-e_{\zeta,k}^{(2,p)}$ of the second eye.

23 Claims, 13 Drawing Sheets

(56) References Cited

U.S. PATENT DOCUMENTS

| | | |
|---|---|---|
| 8,100,530 B2 * | 1/2012 | Zhou et al. .................... 351/205 |
| 2003/0107702 A1 | 6/2003 | Yamakaji |
| 2010/0157242 A1 * | 6/2010 | Esser et al. .................... 351/177 |
| 2010/0296055 A1 | 11/2010 | Esser et al. |
| 2010/0309428 A1 | 12/2010 | Altheimer et al. |

FOREIGN PATENT DOCUMENTS

| | | |
|---|---|---|
| WO | WO-2007/069006 A1 | 6/2007 |
| WO | WO-2008/089995 A1 | 7/2008 |
| WO | WO-2008/089996 A1 | 7/2008 |
| WO | WO 2008/089998 A1 | 7/2008 |

* cited by examiner

Fig.8 – part 1/3

| | -30 | -27.5 | -25 | -22.5 | -20 | -17.5 | -15 | -12.5 |
|---|---|---|---|---|---|---|---|---|
| 25 | | | | | | | | |
| 22.5 | | | | | | | 0.33222 | 0.31051 |
| 20 | | | | | | 0.31632 | 0.28864 | 0.27013 |
| 17.5 | | | | | 0.32735 | 0.26894 | 0.24497 | 0.22338 |
| 15 | | | 0.44097 | 0.35242 | 0.29045 | 0.22671 | 0.19346 | 0.17886 |
| 12.5 | | | 0.41108 | 0.2951 | 0.24747 | 0.21466 | 0.19275 | 0.16584 |
| 10 | | 0.56341 | 0.45553 | 0.18462 | 0.24759 | 0.25768 | 0.23425 | 0.19477 |
| 7.5 | | 1.06786 | 0.88887 | 0.4341 | 0.39884 | 0.37866 | 0.34713 | 0.30513 |
| 5 | | 1.50957 | 1.33613 | 0.73158 | 0.6267 | 0.59134 | 0.55333 | 0.50101 |
| 2.5 | | 1.9585 | 1.76951 | 1.19884 | 1.07458 | 0.99288 | 0.92291 | 0.84628 |
| 0 | 2.72488 | 2.41686 | 2.24167 | 1.63896 | 1.5248 | 1.44427 | 1.38415 | 1.31831 |
| -2.5 | | 2.92296 | 2.74289 | 2.11625 | 2.01 | 1.93431 | 1.90013 | 1.8558 |
| -5 | | 3.30442 | 3.27837 | 2.61622 | 2.51795 | 2.44675 | 2.42998 | 2.41906 |
| -7.5 | | 3.32157 | 3.31882 | 3.12924 | 3.01377 | 2.92789 | 2.90477 | 2.90317 |
| -10 | | 3.34492 | 3.29914 | 3.30143 | 3.30101 | 3.34283 | 3.32869 | 3.25821 |
| -12.5 | | | 3.34552 | 3.32459 | 3.31435 | 3.34031 | 3.40506 | 3.40792 |
| -15 | | | 3.35299 | 3.34843 | 3.32816 | 3.322 | 3.37882 | 3.31855 |
| -17.5 | | | | 3.34764 | 3.32264 | 3.31526 | 3.37457 | 3.17767 |
| -20 | | | | 3.33896 | 3.32607 | 3.3277 | 3.3728 | 3.12799 |
| -22.5 | | | | | 3.32688 | 3.33068 | 3.34797 | 3.13552 |
| -25 | | | | | | 3.32839 | 3.29512 | 3.19663 |
| | | | | | | | 3.29886 | 3.29366 |

Table 1: vertex depth of the back surface of the embodiment

Fig.8 – part 2/3

| | -10 | -7.5 | -5 | -2.5 | 0 | 2.5 | 5 | 7.5 | 10 |
|---|---|---|---|---|---|---|---|---|---|
| 30 | | | | | 0.27721 | | | | |
| 27.5 | 0.32698 | 0.30993 | 0.29125 | 0.27279 | 0.25407 | 0.23396 | 0.21186 | 0.20005 | 0.1097 |
| 25 | 0.2971 | 0.29276 | 0.2818 | 0.27075 | 0.25127 | 0.22883 | 0.1984 | 0.16117 | 0.09555 |
| 22.5 | 0.26448 | 0.26262 | 0.25824 | 0.25016 | 0.23309 | 0.2067 | 0.17254 | 0.15445 | 0.08849 |
| 20 | 0.22134 | 0.22372 | 0.22344 | 0.21687 | 0.20053 | 0.17122 | 0.13452 | 0.09752 | 0.15583 |
| 17.5 | 0.17884 | 0.17982 | 0.17886 | 0.17035 | 0.15288 | 0.12192 | 0.0966 | 0.10196 | 0.19796 |
| 15 | 0.1531 | 0.14197 | 0.12946 | 0.12176 | 0.10205 | 0.07974 | 0.08545 | 0.14933 | 0.27051 |
| 12.5 | 0.16233 | 0.13455 | 0.10934 | 0.07202 | 0.06454 | 0.09211 | 0.13137 | 0.2363 | 0.3773 |
| 10 | 0.25105 | 0.20078 | 0.15059 | 0.06865 | 0.02946 | 0.11673 | 0.23274 | 0.36748 | 0.54085 |
| 7.5 | 0.43534 | 0.36204 | 0.26689 | 0.09269 | 0.02989 | 0.18962 | 0.41067 | 0.58667 | 0.79654 |
| 5 | 0.75524 | 0.64224 | 0.52368 | 0.29034 | 0.0847 | 0.31205 | 0.66184 | 0.93556 | 1.19815 |
| 2.5 | 1.23141 | 1.09725 | 0.9112 | 0.58324 | 0.16268 | 0.50181 | 1.00604 | 1.41103 | 1.74639 |
| 0 | 1.77139 | 1.60173 | 1.35831 | 1.05745 | 0.39117 | 0.63085 | 1.30203 | 1.85646 | 2.31417 |
| -2.5 | 2.34141 | 2.14978 | 1.85573 | 1.4569 | 0.74365 | 0.51771 | 1.36029 | 2.07146 | 2.66478 |
| -5 | 2.83495 | 2.6439 | 2.30462 | 1.79916 | 1.06087 | 0.19901 | 1.18595 | 1.96455 | 2.63956 |
| -7.5 | 3.14726 | 2.93428 | 2.55465 | 1.99037 | 1.2328 | 0.2542 | 0.87027 | 1.67038 | 2.33212 |
| -10 | 3.22396 | 2.95805 | 2.52133 | 1.93247 | 1.23445 | 0.3556 | 0.50331 | 1.28637 | 1.9123 |
| -12.5 | 3.07068 | 2.74729 | 2.25888 | 1.66663 | 1.05286 | 0.30384 | 0.20476 | 0.85233 | 1.44223 |
| -15 | 2.84939 | 2.48467 | 1.9677 | 1.40481 | 0.83355 | 0.25409 | 0.09568 | 0.52539 | 1.06803 |
| -17.5 | 2.72238 | 2.30187 | 1.76109 | 1.21107 | 0.67708 | 0.29328 | 0.15411 | 0.36585 | 0.80762 |
| -20 | 2.68095 | 2.21572 | 1.67902 | 1.12615 | 0.61294 | 0.29366 | 0.17288 | 0.31532 | 0.66345 |
| -22.5 | 2.71239 | 2.2095 | 1.68074 | 1.12556 | 0.60541 | 0.3303 | 0.23704 | 0.31153 | 0.57112 |
| -25 | 2.81193 | 2.27913 | 1.74073 | 1.17513 | 0.63404 | 0.34556 | 0.24875 | 0.27893 | 0.48835 |
| -27.5 | 2.97958 | 2.41435 | 1.85707 | 1.27501 | 0.69398 | 0.34463 | 0.18368 | 0.22846 | 0.53166 |
| -30 | | | | | 0.80373 | | | | |

Table 1: (cont.)

Fig.8 – part 3/3

| | 12.5 | 15 | 17.5 | 20 | 22.5 | 25 | 27.5 | 30 |
|---|---|---|---|---|---|---|---|---|
| 25 | 0.17608 | 0.27027 | | | | | | |
| 22.5 | 0.22376 | 0.28247 | | | | | | |
| 20 | 0.23367 | 0.32601 | 0.34257 | | | | | |
| 17.5 | 0.29249 | 0.38882 | 0.39356 | 0.46308 | | | | |
| 15 | 0.38677 | 0.48915 | 0.47443 | 0.53646 | 0.58698 | | | |
| 12.5 | 0.51508 | 0.62308 | 0.57363 | 0.63195 | 0.67122 | 0.69402 | | |
| 10 | 0.69838 | 0.80874 | 0.69911 | 0.75171 | 0.77819 | 0.79015 | | |
| 7.5 | 0.97115 | 1.08049 | 0.8799 | 0.92048 | 0.93695 | 0.94407 | 1.11766 | |
| 5 | 1.38421 | 1.49282 | 1.1477 | 1.18964 | 1.23768 | 1.3403 | 1.49313 | |
| 2.5 | 1.94655 | 2.02812 | 1.56192 | 1.61501 | 1.66973 | 1.75831 | 1.88786 | |
| 0 | 2.56692 | 2.62416 | 2.05853 | 2.07752 | 2.11326 | 2.18525 | 2.29426 | |
| -2.5 | 3.05693 | 3.18702 | 2.59163 | 2.5513 | 2.55365 | 2.60625 | 2.6838 | 2.87446 |
| -5 | 3.20501 | 3.54665 | 3.13201 | 3.03676 | 2.98397 | 3.00112 | 3.08941 | |
| -7.5 | 2.99045 | 3.57474 | 3.59948 | 3.50087 | 3.43532 | 3.42408 | 3.49288 | |
| -10 | 2.58906 | 3.30954 | 3.85191 | 3.87283 | 3.72308 | 3.58091 | 3.47107 | |
| -12.5 | 2.10938 | 2.8859 | 3.80001 | 3.92848 | 3.73408 | 3.59482 | 3.51238 | |
| -15 | 1.69011 | 2.4643 | 3.49138 | 3.79671 | 3.70332 | 3.59928 | | |
| -17.5 | 1.40592 | 2.16171 | 3.15214 | 3.57983 | 3.69056 | 3.57305 | | |
| -20 | 1.25138 | 1.98959 | 2.88996 | 3.37874 | 3.6561 | | | |
| -22.5 | 1.16913 | 1.90323 | 2.69927 | 3.24736 | | | | |
| -25 | 1.13261 | 1.84208 | 2.57753 | | | | | |

Table 1: (cont.)

OPTIMIZATION AND PRODUCTION OF AN EYEGLASS LENS FOR CORRECTING AN ASTIGMATIC REFRACTION

The disclosure herein relates to a method for optimizing and producing at least one spectacle lens, in particular a spectacle lens pair, for correcting at least an astigmatic refraction of a first eye of a spectacle wearer, in particular for correcting a first astigmatic refraction of the first eye by a first spectacle lens of the spectacle lens pair and a second astigmatic refraction of a second eye of the spectacle wearer by a second spectacle lens of the spectacle lens pair. Moreover, the disclosure herein relates to at least one spectacle lens, in particular a spectacle lens pair, to be used in a specific situation of wear, for correcting at least an astigmatic refraction of a first eye of a spectacle wearer, in particular for correcting a first astigmatic refraction of the first eye and a second astigmatic refraction of a second eye of the spectacle wearer, a computer program product, a storage medium, and an apparatus for producing at least one spectacle lens, in particular a spectacle lens pair, for correcting at least an astigmatic refraction of a first eye of a spectacle wearer, in particular for correcting a first astigmatic refraction of the first eye and a second astigmatic refraction of a second eye of the spectacle wearer.

BACKGROUND

For the production or optimization of spectacle lenses, in particular of individual spectacle lenses, each spectacle lens is manufactured such that the best possible correction of a refractive error of the respective eye of the spectacle wearer is obtained for each desired direction of sight or each desired object point. In general, a spectacle lens is said to be fully corrective for a given direction of sight if the values sphere, cylinder, and axis of the wavefront upon passing the vertex sphere match with the values for sphere, cylinder, and axis. However, a full correction for all directions of sight at the same time is normally not possible. Therefore, the spectacle lenses are manufactured such that they achieve a good correction of visual defects of the eye and only small aberrations especially in central visual regions, while larger aberrations are permitted in peripheral regions. These aberrations depend on the type and scope of the necessary corrections as well as on the position of the spectacle lens, i.e. the respective visual point.

In particular for a correction of an astigmatic refraction of an eye, in addition to knowing the amount of the astigmatic refraction, i.e. the value of the cylinder, the axial position thereof is decisive as well. In order to be able to correct an astigmatic refraction of the eye, these values are therefore measured for the eye to be corrected while the eye is in a measurement position or reference direction of sight, in particular the zero direction of sight. Here, preferably a coordinate system is specified, and the axial position of the astigmatic refraction with respect to this coordinate system is determined. The amount of the astigmatism can be indicated as the difference of the main refractive powers. The coordinate system may be a Cartesian coordinate system with the axes $e_x$, $e_y$, and $e_z$, its point of origin particularly being in the ocular center of rotation of the eye to be corrected. The axis $e_z$ is preferably parallel to the reference direction of sight, in particular to the zero direction of sight, and is oriented in the direction of the main ray. Preferably, the axis $e_z$ is a horizontal axis, which with respect to the eye faces backward in the zero direction of sight, i.e. in the direction of the light ray. The axis $e_x$ runs e.g. horizontally and perpendicularly to the axis $e_z$, in particular perpendicularly to the reference direction of sight or zero direction of sight. Finally, the axis $e_y$ runs perpendicularly to the two other axes and is in particular vertically oriented upward. Thus, the three axes $e_x$, $e_y$, and $e_z$ for example form a base coordinate system, in which also the axial position of an astigmatism to be corrected can be described.

When looking through a spectacle lens, the eye pair continuously performs eye movements, whereby the visual points change within the spectacle lens. Thus, eye movements always result in changes of the imaging properties, in particular of the aberrations for the spectacle lens. Furthermore, during eye movements, each eye performs a torsion about the momentary axis of the direction of sight, which in particular depends on the direction of sight itself. In the case of an astigmatic refraction of the eye, this often leads to an unsatisfactory correction of the astigmatism especially in the near zone.

SUMMARY

The disclosure herein provides a method and a computer program product for optimizing and producing at least a first spectacle lens, in particular a spectacle lens pair, in particular for correcting an astigmatic refraction with improved optical properties in particular for use of the spectacle lens or the spectacle lens pair in near vision.

Specifically, the disclosure herein provides a method for optimizing and producing at least a first spectacle lens for a specific situation of wear for correcting at least a first astigmatic refraction (or a first vectorial astigmatic refraction) of a first eye of a spectacle wearer, which in a reference direction of sight $-e_z^{(1)}$ of the first eye has a first cylinder value and a first axial position or cylinder reference axis $\alpha_0^{(1)}$, i.e. a cylinder axis of the eye refraction of the first eye, when the first eye is positioned in the reference direction of sight of the first eye, comprising at least a primary calculation or optimization step of the first spectacle lens, i.e. of at least one surface of a surface area of the first spectacle lens (therefore also referred to as a first primary calculation or optimization step), which comprises:

determining a primary direction of sight $-e_\zeta^{(1,p)}$ of the first eye, which in particular deviates from the reference direction of sight $-e_z^{(1)}$ of the first eye (therefore also referred to as a first primary direction of sight $-e_\zeta^{(1,p)}$), for at least one primary evaluation point $i_b^{(1,p)}$ of the first spectacle lens (therefore also referred to as a first primary evaluation point $i_b^{(1,p)}$); and determining a corresponding primary direction of sight $-e_{\zeta,k}^{(2,p)}$ of a second eye of the spectacle wearer, which corresponds to the primary direction of sight $-e_\zeta^{(1,p)}$ of the first eye in the specific situation of wear (therefore also referred to as a corresponding second primary direction of sight $-e_{\zeta,k}^{(2,p)}$), in particular depending on starting values for a second spectacle lens in particular intended to be used with the first spectacle lens in a spectacle lens pair. Thus, preferably a second spectacle lens, which in particular has not yet been optimized according to the exemplary embodiment, is used as a starting value for determining the corresponding primary direction of sight of the second eye, which corresponds to the determined primary direction of sight of the first eye, on the basis of the predetermined second spectacle lens for the specific situation of wear. Preferably, this is done using a ray tracing method. Thereby, in particular the local, i.e. direction of sight-dependent prismatic power of the first and/or the second spectacle lens in a specific situation of wear is taken into account for the calculation of the first spectacle lens.

Moreover, the first primary calculation or optimization step comprises minimizing a primary merit function for at least one surface of the first spectacle lens (therefore also referred to as a first primary merit function), wherein in the first primary merit function for the at least one primary evaluation point $i_b^{(1,p)}$ of the first spectacle lens, a correction of a first primary transformed astigmatic refraction or of a first primary transformed vectorial astigmatic refraction (an astigmatic refraction or a vectorial astigmatic refraction particularly being understood to be the pair of a cylinder value and a unit vector as the axis, which lies in the plane perpendicular to the direction of sight and faces in the direction of the axial position of the astigmatism) by the first spectacle lens in the specific situation of wear is taken into account or evaluated such that the first primary transformed astigmatic refraction depends on the determined corresponding primary direction of sight $-e_{\zeta,k}^{(2,p)}$ of the second eye, i.e. has different values for at least two different corresponding primary directions of sight $-e_{\zeta,k}^{(2,p)}$ of the second eye, as they might result for different starting values of the second spectacle lens.

Preferably, a stationary or object-fixed base coordinate system for the respective eye is specified, as has been described above by way of example. In the respective base coordinate system, preferably the cylinder axis of an astigmatic refraction of the respective eye, i.e. of the first and/or the second eye, is individually determined in the reference direction of sight by an optician or ophthalmologist for a patient or spectacle wearer and provided as the cylinder reference axis for the method for optimizing and producing at least the first spectacle lens, in particular the spectacle lens pair, for correcting the respective astigmatic refraction. In a preferred embodiment, the reference direction of sight of the first and/or the second eye is the respective zero direction of sight and goes horizontally straight on into the distance or into infinity. It is thus parallel to the third base coordinate axes $e_z^{(1)}$ and $e_z^{(2)}$ of the first and second eyes, respectively, wherein it is oppositely oriented in a preferred convention, which is to be expressed by the minus sign. This convention is to apply to the first and second primary directions of sight as well, which is why these directions of sight are parallel to the respective eye-side main ray and are oriented oppositely thereto. The respective cylinder axis can be expressed with respect to the other two coordinate axes, for example.

Thus, starting from the astigmatic refraction of the first eye to be corrected in the reference direction of sight, which can be measured or determined by an optician in the known manner, for example, a transformation, which depends on the corresponding direction of sight of the second eye in the specific situation of wear particularly taking the second spectacle lens in its position in front of the second eye of the spectacle wearer into account, is performed in order to obtain the transformed astigmatic refraction. Preferably, the transformed astigmatic refraction is indicated as the astigmatic refraction in the reference direction of sight in the form of a cylinder value (in particular as a scalar variable with the unit D) and an axial position (e.g. in the form of a transformed angle relative to a torsion reference axis of the first direction of sight). For the calculation and optimization of the first spectacle lens, this transformed astigmatic refraction is then taken into account in the merit function, in particular the first primary merit function, as the refraction of the eye to be corrected in the direction of sight belonging to the first evaluation point.

Preferably, the disclosure herein relates to a method for optimizing and producing the first spectacle lens for a pair of spectacle lenses to be used together with a second spectacle lens of the pair of spectacle lenses in spectacles for the specific situation of wear, wherein determining the corresponding primary direction of sight $-e_{\zeta,k}^{(2,p)}$ of the second eye comprises determining a corresponding primary evaluation point $i_b^{(2,p)}$ of the second spectacle lens, which corresponds to the primary evaluation point $i_b^{(1,p)}$ of the first spectacle lens in the specific situation of wear, taking into account a prismatic power of the first spectacle lens and/or of the second spectacle lens, to be optimized, in the primary evaluation point of the first or the second spectacle lens, respectively, in the specific situation of wear.

The method preferably comprises detecting a second cylinder reference axis $\alpha_0^{(2)}$ of a second astigmatic refraction of the second eye in a reference direction of sight $-e_z^{(2)}$ of the second eye, wherein the first primary merit function for the at least one surface of the first spectacle lens depends on a correction of a second primary transformed astigmatic refraction by the second spectacle lens in the specific situation of wear, wherein the second primary transformed astigmatic refraction has a second primary cylinder correction axis $\alpha_K^{(2,p)}$, which encloses a second primary correction torsion angle $\psi_K^{(2,p)}$ with a second primary torsion reference axis $e_L^{(2,p)}$, which is perpendicular both to the reference direction of sight $-e_z^{(2)}$ of the second eye and to the corresponding primary direction of sight $-e_{\zeta,k}^{(2,p)}$ of the second eye, said second primary correction torsion angle $\psi_K^{(2,p)}$ deviating from a second primary reference torsion angle $\psi_0^{(2,p)}$ between the second cylinder reference axis $\alpha_0^{(2)}$ and the second primary torsion reference axis $e_L^{(2,p)}$ by a second primary torsion correction angle $\psi_\Delta^{(2,p)}(e_\zeta^{(1,p)})$, which at least depends on the determined primary direction of sight $-e_\zeta^{(1,p)}$ of the first eye.

Preferably, the second primary torsion correction angle depends both on the primary direction of sight of the first eye and on the primary direction of sight of the second eye. Particularly preferably, it holds that: $\psi_\Delta^{(2)}=-\psi_\Delta^{(1)}$, particularly $\psi_\Delta^{(2,p)}=-\psi_\Delta^{(1,p)}$, particularly preferably, a mean value of torsion angles is formed particularly in Helmholtz coordinates or other coordinates suitable for representing torsion.

In a preferred embodiment, the second spectacle lens is known prior to the optimization of the first lens to be produced and remains unchanged in the optimization. In the evaluation of the merit function for each point or each evaluation point of the lens to be optimized, the corresponding visual point of the lens, which remains unchanged, is calculated, so that the Helmholtz angles can be determined therefrom. For the calculation of the deviation between desired and actual values of the astigmatism in the merit function, the torsional position of the eye is preferably determined according to equations (8) and (9).

Preferably, the disclosure herein relates to a method for optimizing and producing a spectacle lens pair for a specific situation of wear for correcting a first astigmatic refraction of a first eye of a spectacle wearer, which in a reference direction of sight $-e_z^{(1)}$ of the first eye has a first cylinder value and a first axial position or cylinder reference axis $\alpha_0^{(1)}$, i.e. a cylinder axis of the eye refraction of the first eye, when the first eye is positioned in the reference direction of sight of the first eye, by a first spectacle lens of the spectacle lens pair, and a second astigmatic refraction of a second eye of the spectacle wearer, which in a reference direction of sight $-e_z^{(2)}$ of the second eye has a second cylinder value and a second axial position or cylinder reference axis $\alpha_0^{(2)}$, i.e. a cylinder axis of the eye refraction of the second eye if the second eye is positioned in the reference direction of sight of the second eye, by a second spectacle lens of the spectacle lens pair, comprising a primary calculation or optimization step of the first spectacle lens, i.e. of at least one surface of a surface area of the first spectacle lens (therefore also referred to as a first primary calculation or optimization step), which comprises:

determining a primary direction of sight $-e_\zeta^{(1,p)}$ of the first eye, which in particular deviates from the reference direction of sight $-e_z^{(1)}$ of the first eye (therefore also referred to as a first primary direction of sight $-e_\zeta^{(1,p)}$), for at least one primary evaluation point $i_b^{(1,p)}$ of the first spectacle lens (therefore also referred to as a first primary evaluation point $i_b^{(1,p)}$); and determining a corresponding primary direction of sight $-e_{\zeta,k}^{(2,p)}$ of the second eye of the spectacle wearer, which corresponds to the primary direction of sight $-e_\zeta^{(1,p)}$ of the first eye in the specific situation of wear (therefore also referred to as a corresponding second primary direction of sight $-e_{\zeta,k}^{(2,p)}$), depending on starting values for the second spectacle lens.

Furthermore, the method preferably comprises a secondary calculation or optimization step of the second spectacle lens, i.e. of at least one surface or a surface area of the second spectacle lens (therefore also referred to as a second secondary calculation or optimization step), depending on the first spectacle lens determine d in the first primary calculation or optimization step. Thus, in particular the starting value for the second spectacle lens is changed and optimized taking the first spectacle lens determined in the first primary calculation or optimization step into account. Preferably, the calculation or optimization of the second spectacle lens is performed by analogy with the calculation or optimization of the first spectacle lens, wherein the first spectacle lens determined in the first primary calculation or optimization step is correspondingly taken into consideration in the calculation or optimization of the second spectacle lens in an analogous manner, just like the starting value of the second spectacle lens in the calculation or optimization of the first spectacle lens. Here, preferably a second secondary merit function is minimized.

In the optimization, the first primary or the second secondary merit function particularly evaluates local values of the refraction deficit of the first or the second spectacle lens in a multitude of evaluation points of the respective spectacle lens, i.e. for a multitude of different directions of sight of the associated eye in the specific situation of wear. Preferably, for each evaluation point of the corresponding spectacle lens, the direction of sight of the respective eye corresponding to the specific situation of wear is determined on the one hand, and on the other hand, preferably for each evaluation point, an astigmatic refraction of the first or the second eye, which corresponds to the determined direction of sight but is corrected or transformed for the situation of wear with respect to a corresponding eye movement of the other eye on the basis of a desired value of the second spectacle lens or the determined first spectacle lens, is taken into account. This leads to an especially good binocular tolerability of a thus optimized and produced spectacle lens pair particularly for use in near vision.

Hence, particularly an optimization or production of at least one spectacle lens, preferably of a spectacle lens pair, is achieved by a successive monocular calculation or optimization of individual spectacle lenses, wherein in the respective monocular calculation or optimization step (primary and/or secondary calculation or optimization step) for one of the two spectacle lenses, the other spectacle lens is taken into account, but remains unchanged until in particular a desired or predetermined convergence of a monocular optimization method, in particular in the first primary calculation or optimization step, is reached for said one spectacle lens. A very efficient and fast production of a spectacle lens, in particular of a spectacle lens pair, is achieved thereby. Here, the cylinder prescriptions are taken into account preferably for both spectacle lenses of the spectacle lens pair. Even though the method for optimizing and producing a first spectacle lens and for optimizing and producing a spectacle lens pair preferably changes the coupled degrees of freedom of two lenses and thereby improves binocular vision, the effort, in particular the numeral effort, of the method involves only the effort of a few monocular optimizations.

BRIEF DESCRIPTION OF THE DRAWINGS

In the following, the disclosure herein will be described with reference to the figures, which show:

FIG. 8 illustrates a table of the vertex depths of the back surface of the spectacle lens according to the embodiments of FIGS. 7A-7D.

DETAILED DESCRIPTION

Figure 1:
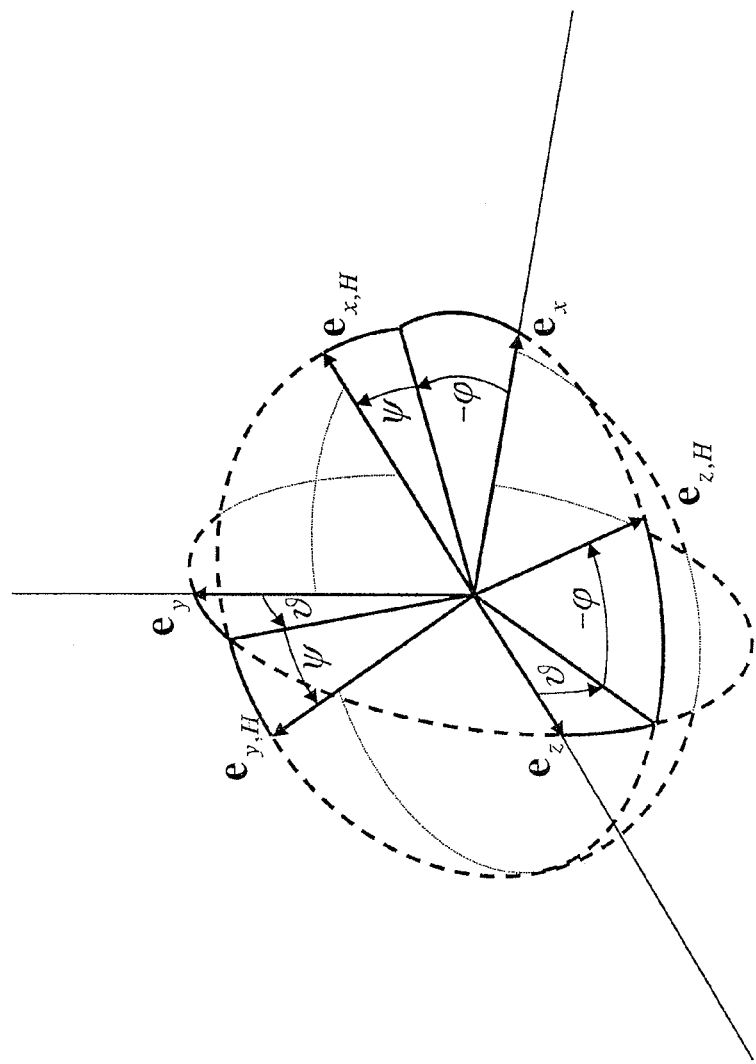
FIG. 1 illustrates an exemplary representation of Helmholtz coordinates according to a preferred embodiment.

For the respective numbering or designation of individual calculation or optimization steps, respective axes, directions, and angles, the following conventions, which are summarized at a glance for a better understanding, will be used in the present description of the exemplary embodiments thereof:

Vectors and directions are indicated in bold type, while scalars and indices are indicated in normal type (i.e. not bold).

The method steps, axes, directions, angles, refraction variables, etc. relating to the first eye, spectacle lens, or base coordinate system are either provided with the addition "of the first eye" or "of the first spectacle lens", or may be preceded by "first". In the mathematical representation, they are provided with a superscript "1" (in brackets).

The method steps, axes, directions, angles, refraction variables, etc. relating to the second eye, spectacle lens, or base coordinate system are either provided with the addition "of the second eye" or "of the second spectacle lens", or may be preceded by "second". In the mathematical representation, they are provided with a superscript "2" (in brackets).

The successively performed calculation or optimization steps are provided with the addition "primary" for designating a first one of a plurality of successive steps (calculation or optimization steps) according to the embodiments disclosed herein. The variables determined or considered in this step (in particular axes, directions, angles, etc.), particularly as far as their values in the respective step might differ from the corresponding values in a later step, are also provided with the designation "primary". In the mathematical representation, they are provided with a superscript "p" (in brackets).

"secondary" for designating a further or second step (calculation or optimization step), according to the embodiments disclosed herein, after the first, in particular following the first, i.e. "primary" step. The variables determined or considered in this step (in particular axes, directions, angles, etc.), particularly as far as their values in the respective step might differ from the corresponding values in another (e.g. earlier or later) step, are also provided with the designation "secondary". In the mathematical representation, they are provided with a superscript "s" (in brackets).

By analogy, further steps and variables may have the designations "tertiary", "quarternary", etc., with corresponding superscripts "t" or "q".

Where it is not of importance in the individual case as to which eye or spectacle lens or as to which one of a plurality of calculation or optimization steps a further characterization of a variable in conformity with a preferred embodiment relates, i.e. if such a characterization can be equally applied to each eye or spectacle lens or to each calculation or optimization step, the defined designation or the corresponding index can be omitted for the corresponding variable.

The direction respectively referred to as the corresponding direction of sight is provided with a subscript "k"

Preferably, in the first primary merit function for the at least one primary evaluation point $i_b^{(1,p)}$ of the first spectacle lens, the correction of a first primary transformed astigmatic refraction by the first spectacle lens in the specific situation of wear is taken into account such that the first primary transformed astigmatic refraction with respect to the primary direction of sight of the first eye has the first cylinder value and a first primary cylinder correction axis $\alpha_K^{(1,p)}$ (i.e. cylinder axis of the eye refraction when the first eye is positioned in the first primary direction of sight) or is specified by the first cylinder value and a first primary cylinder correction axis $\alpha_K^{(1,p)}$, wherein the first primary cylinder correction axis $\alpha_K^{(1,p)}$ encloses a first primary correction torsion angle $\psi_K^{(1,p)}$ with a first primary torsion reference axis $e_L^{(1,p)}$, which is perpendicular both to the reference direction of sight $-e_z^{(1)}$ of the first eye and to the primary direction of sight $-e_\zeta^{(1,p)}$ of the first eye, said first primary correction torsion angle $\psi_K^{(1,p)}$ deviating from a first primary reference torsion angle $\psi_0^{(1,p)}$ between the first cylinder reference axis $\alpha_0^{(1)}$ and the first primary torsion reference axis $e_L^{(1,p)}$ by a first primary torsion correction angle $\psi_A^{(1,p)}(e_{\zeta,k}^{(2,p)})$, which at least depends on the determined corresponding primary direction of sight $-e_{\zeta,k}^{(2,p)}$ of the second eye, i.e. has different values for at least two different corresponding primary directions of sight $-e_{\zeta,k}^{(2,p)}$ of the second eye, as they might result for different starting values of the second spectacle lens and/or for different situations of wear.

In the optimization, the first primary merit function evaluates particularly local values of the refraction deficit of the first spectacle lens in a multitude of evaluation points of the spectacle lens, i.e. for a multitude of different directions of sight of the first eye in the specific situation of wear. In doing so, preferably for each evaluation point of the first spectacle lens, the direction of sight of the first eye corresponding to the specific situation of wear is determined on the one hand, and on the other hand, preferably for each evaluation point, an axial position of the astigmatic refraction of the first eye, which corresponds to the determined direction of sight but is corrected for the situation of wear with respect to the second eye, is taken into account. Here, a model is taken as a basis for the torsion adjustment of the first eye, which in addition depends on the direction of sight of the second eye. This leads particularly to an improvement of the optical properties of the spectacle lens in the near zone, in which the influence of the second eye on the torsional movement of the first eye is particularly large. Thus, in particular binocular vision is improved in the near zone.

As far as the second secondary calculation or optimization step is performed by analogy with the first primary calculation or optimization step in a preferred embodiment, the second secondary calculation or optimization step thus preferably comprises:

determining a secondary direction of sight $-e_\zeta^{(2,s)}$ of the second eye (therefore also referred to as a second secondary direction of sight $-e_\zeta^{(2,s)}$) for at least one secondary evaluation point $i_b^{(2,s)}$ of the second spectacle lens (therefore also referred to as a second secondary evaluation point $i_b^{(2,s)}$);

determining a corresponding secondary direction of sight $-e_{\zeta,k}^{(1,s)}$ of the first eye of the spectacle wearer, which corresponds to the secondary direction of sight $-e_\zeta^{(2,s)}$ of the second eye in the specific situation of wear (therefore also referred to as a corresponding first secondary direction of sight $-e_{\zeta,k}^{(1,s)}$), depending on the first spectacle lens determined in the first primary calculation or optimization step; and minimizing a secondary merit function for at least one surface of the second spectacle lens (therefore also referred to as a second secondary merit function), wherein in the second secondary merit function for the at least one secondary evaluation point $i_b^{(2,s)}$ of the second spectacle lens, a correction of a second secondary transformed astigmatic refraction by the second spectacle lens in the specific situation of wear is taken into account such that the second secondary transformed astigmatic refraction with respect to the secondary direction of sight of the second eye has the second cylinder value and a second secondary cylinder correction axis $\alpha_K^{(2,s)}$ (i.e. cylinder axis of the eye refraction when the second eye is positioned in the second secondary direction of sight) or is specified by the second cylinder value and a second secondary cylinder correction axis $\alpha_K^{(2,s)}$, wherein the second secondary cylinder correction axis $\alpha_K^{(2,s)}$ encloses a second secondary correction torsion angle $\psi_K^{(2,s)}$ with a second secondary torsion reference axis $e_L^{(2,s)}$, which is perpendicular both to the reference direction of sight $-e_z^{(2)}$ of the second eye and to the secondary direction of sight $-e_\zeta^{(2,s)}$ of the second eye, said second secondary correction torsion angle $\psi_K^{(2,s)}$ deviating from a second secondary reference torsion angle $\psi_0^{(2,s)}$ between the second cylinder reference axis $\alpha_0^{(2)}$ and the second secondary torsion reference axis $e_L^{(2,s)}$ by a second secondary torsion correction angle $\psi_A^{(2,s)}(e_{\zeta,k}^{(1,s)})$, which at least depends on the determined corresponding secondary direction of sight $-e_{\zeta,k}^{(1,s)}$ of the first eye, i.e. has different values for at least two different corresponding secondary directions of sight $-e_{\zeta,k}^{(1,s)}$ of the first eye, as they might result for different first spectacle lenses determined in the first primary calculation or optimization step and/or for different situations of wear.

In another preferred embodiment, the second secondary calculation or optimization step of the second spectacle lens comprises copying at least one surface of the first spectacle lens determined in the first primary calculation or optimization step. Here, the second spectacle lens or at least one surface of the second spectacle lens is determined in particular by copying and mirroring for example vertex depths or other coefficients for describing the determined first spectacle lens or the at least one surface of the first spectacle lens. This is particularly advantageous if the refractions of the two eyes of the spectacle wearer are symmetric or mirror-symmetric or have symmetric or mirror-symmetric deficits. Such copying and mirroring can in particular be performed as a last calculation or optimization step of a multitude of successively performed calculation or optimization steps.

In a further preferred embodiment, the method comprises:
a primary calculation or optimization step of the second spectacle lens (therefore also referred to as a second primary calculation or optimization step) depending on starting values for the first spectacle lens; and
a secondary calculation or optimization step of the first spectacle lens (therefore also referred to as a first secondary calculation or optimization step) depending on the first spectacle lens determined in the second primary calculation or optimization step.

Particularly preferably, the second primary calculation or optimization step comprises:
determining a primary direction of sight $-e_\zeta^{(2,p)}$ of the second eye (therefore also referred to as a second primary direction of sight $-e_\zeta^{(2,p)}$ for at least one primary evaluation point $i_b^{(2,p)}$ of the second spectacle lens (therefore also referred to as a second primary evaluation point $i_b^{(2,p)}$); and
determining a corresponding primary direction of sight $-e_{\zeta,k}^{(1,p)}$ of the first eye of the spectacle wearer, which corresponds to the primary direction of sight $-e_\zeta^{(2,p)}$ of the second eye in the specific situation of wear (therefore also referred to as a corresponding first primary direction of sight $-e_{\zeta,k}^{(1,p)}$) depending on starting values for a first spectacle lens. Thus, preferably a first spectacle lens, which in particular has not yet been optimized according to the exemplary embodiment, is used as a starting value for determining the corresponding primary direction of sight of the first eye, which corresponds to the determined primary direction of sight of the second eye, on the basis of the predetermined first spectacle lens for the specific situation of wear. Preferably, this is done using a ray tracing method. Thereby, in particular the local, i.e. direction of sight-dependent prismatic power of the first and/or the second spectacle lens in the specific situation of wear is taken into account for the calculation of the second spectacle lens.

Preferably, the second primary calculation or optimization step further comprises minimizing a primary merit function for at least one surface of the second spectacle lens (therefore also referred to as a second primary merit function), wherein in the second primary merit function for the at least one primary evaluation point $i_b^{(2,p)}$ of the second spectacle lens, a correction of a second primary transformed astigmatic refraction by the second spectacle lens in the specific situation of wear is taken into account such that the second primary transformed astigmatic refraction with respect to the primary direction of sight of the second eye has the second cylinder value and a second primary cylinder correction axis $\alpha_K^{(2,p)}$ (i.e. cylinder axis of the eye refraction when the second eye is positioned in the second primary direction of sight) or is specified by the second cylinder value and a second primary cylinder correction axis $\alpha_K^{(2,p)}$, wherein the second primary cylinder correction axis $\alpha_K^{(2,p)}$ encloses a second primary correction torsion angle $\psi_K^{(2,p)}$ with a second primary torsion reference axis $e_L^{(2,p)}$, which is perpendicular both to the reference direction of sight $-e_z^{(2)}$ of the second eye and to the primary direction of sight $-e_\zeta^{(2,p)}$ of the second eye, said second primary correction torsion angle $\psi_K^{(2,p)}$ deviating from a second primary reference torsion angle $\psi_0^{(2,p)}$ between the second cylinder reference axis $\alpha_0^{(2)}$ and the second primary torsion reference axis $e_L^{(2,p)}$ by a second primary torsion correction angle $\psi_A^{(2,p)}(e_{\zeta,k}^{(1,p)})$, which at least depends on the determined corresponding primary direction of sight $-e_{\zeta,k}^{(1,p)}$ of the first eye, i.e. has different values for at least two different corresponding primary directions of sight $-e_{\zeta,k}^{(1,p)}$ of the first eye, as they might result for different starting values of the first spectacle lens and/or for different situations of wear.

Alternatively or in addition, the first secondary calculation or optimization step preferably comprises:
determining a secondary direction of sight $-e_\zeta^{(1,s)}$ of the first eye (therefore also referred to as a first secondary direction of sight $-e_\zeta^{(1,s)}$) for at least one secondary evaluation point $i_b^{(1,s)}$ of the first spectacle lens (therefore also referred to as a first secondary evaluation point $i_b^{(1,s)}$);
determining a corresponding secondary direction of sight $-e_{\zeta,k}^{(2,s)}$ of the second eye of the spectacle wearer, which corresponds to the secondary direction of sight $-e_\zeta^{(1,s)}$ of the first eye in the specific situation of wear (therefore also referred to as a corresponding second secondary direction of sight $-e_{\zeta,k}^{(2,s)}$), depending on the second spectacle lens determined in the second primary calculation or optimization step; and
minimizing a secondary merit function for at least one surface of the first spectacle lens (therefore also referred to as a first secondary merit function), wherein in the first secondary merit function for the at least one secondary evaluation point $i_b^{(1,s)}$ of the first spectacle lens, a correction of a first secondary transformed astigmatic refraction by the first spectacle lens in the specific situation of wear is taken into account such that the first secondary transformed astigmatic refraction with respect to the secondary direction of sight of the first eye has the first cylinder value and a first secondary cylinder correction axis $\alpha_K^{(1,s)}$ (i.e. cylinder axis of the eye refraction when the first eye is positioned in the first secondary direction of sight) or is specified by the first cylinder value and a first secondary cylinder correction axis $\alpha_K^{(1,s)}$, wherein the first secondary cylinder correction axis $\alpha_K^{(1,s)}$ encloses a first secondary correction torsion angle $\psi_K^{(1,s)}$ with a first secondary torsion reference axis $e_L^{(1,s)}$, which is perpendicular both to the reference direction of sight $-e_z^{(1)}$ of the first eye and to the secondary direction of sight $-e_\zeta^{(1,s)}$ of the first eye, said first secondary correction torsion angle $\psi_K^{(1,s)}$ deviating from a first secondary reference torsion angle $\psi_0^{(1,s)}$ between the first cylinder reference axis $\alpha_0^{(1)}$ and the first secondary torsion reference axis $e_L^{(1,s)}$ by a first secondary torsion correction angle $\psi_\Delta^{(1,s)}(e_{\zeta,k}^{(2,s)})$, which at least depends on the determined corresponding secondary direction of sight $-e_{\zeta,k}^{(2,s)}$ of the second eye, i.e. has different values for at least two different corresponding secondary directions of sight $-e_{\zeta,k}^{(2,s)}$ of the second eye, as they might result for different second spectacle lenses determined in the second primary calculation or optimization step and/or for different situations of wear.

Preferably, eye torsion, particularly of the first eye, is taken into account in a merit function of a spectacle lens, particularly in the first primary merit function, by a torsion correction angle $\psi_\Delta^{(1)}(e_\zeta^{(2)})$ particularly the first primary torsion correction angle $\psi_\Delta^{(1,p)}(e_{\zeta,k}^{(2,p)})$. Thereby, an especially efficient and exact optimization for the specific situation of wear can be achieved for the spectacle lens pair. The minimization of the merit function is preferably performed by varying at least one surface of the respective spectacle lens and evaluating the optical properties of the spectacle lens in the specific situation of wear until the value of the merit function has fallen below a predetermined threshold value or until the value of the merit function between successive evaluation steps or recursion steps does not change any more or changes less than a predetermined threshold value. Such a threshold value can be defined as a termination criterion for the calculation or optimization step.

For a predetermined position of wear of the first spectacle lens or the spectacle lens pair or of spectacles for a spectacle wearer, i.e. for a predetermined position of the spectacle lens or the spectacle lenses in front of the eyes of the spectacle wearer, and a predetermined object distance, a corresponding pair of directions of sight of the first and left eyes results for many object points, which generally are not arranged symmetrically and during eye movements change depending on the object position and depending on the first spectacle lens and possibly a second spectacle lens. Thus, not only every single direction of sight, but in particular also the relation of the two directions of sight to each other depends on the situation of wear and the first and second spectacle lenses. Due to the preferred consideration of the influence of the situation of wear on the torsion of the first eye on the basis of the corresponding directions of sight determined in the situation of wear, an improved correction of astigmatic refractions across a broad range of use of a spectacle lens, in particular also in the near zone, can be achieved.

The situation of wear specifies a positioning of the spectacle lens or the spectacle lenses in front of the eyes of the spectacle wearer and an object distance model. Thus, as the situation of wear, in particular data of wear relating to a positioning of the spectacle lenses for a spectacle wearer and relating to a visual task of the spectacle wearer are gathered and provided. Such data of wear preferably comprise frame data, in particular with respect to a box dimension of the frame lenses or frame spectacle lens shapes and/or the bridge width and/or a face form angle and/or a forward inclination etc. of the spectacles. In a preferred embodiment, the data of wear relating to a visual task comprise a specification on mainly used viewing angle zones and/or mainly used object distances.

In any case, the specific situation of wear for a multitude of directions of sight of at least one eye of the spectacle wearer uniquely specifies the position of an associated object point such that the visual ray of the other eye when looking at the same object point (depending on the optical power of the associated spectacle lens) is uniquely specified as well. The two visual rays (for the left and right eyes) belonging to an object point are referred to as corresponding visual rays. Respective penetration points of the corresponding visual rays through the two spectacle lenses are referred to as corresponding visual points. Here, each visual point can represent an evaluation point for the spectacle lens on the front and/or the back surface of a spectacle lens. Due to the clear assignment of the visual rays and object points to the visual points through the corresponding spectacle lens, the respective evaluation point might also be represented by the corresponding visual ray or the direction of sight and/or the object point. In a preferred embodiment, the evaluation points of a spectacle lens are represented by two coordinates of a coordinate system specified with respect to the spectacle lens. To this end, preferably a Cartesian x-y-z coordinate system is specified, the origin of which e.g. being in the geometric center (of the uncut or raw-round first or the second spectacle lens) or in the lens center of the first or the second spectacle lens in particular on the front surface thereof, wherein the y axis extends in the vertical direction in the position of wear or situation of wear, and the z axis faces toward the eye. Thus, the evaluation points can in particular be represented by the x-y coordinates of the visual points.

Pairs of evaluation points of the left and the right spectacle lens, which represent corresponding visual points, are referred to as corresponding evaluation points. The corresponding evaluation points relate to a common object point viewed by both eyes at the same time, which is why the corresponding evaluation points depend on the specific situation of wear.

Depending on the desired application or objective, the first or the second spectacle lens or the spectacle lens pair to be optimized or the spectacle lenses of the spectacle lens pair can be produced or optimized for a predetermined or predeterminable situation of wear of an average or individually determined spectacle wearer.

An average situation of wear (as defined in DIN 58 208 part 2) can be characterized by:
  parameters of a standard eye, such as the so-called Gullstrand's schematic eye of a spectacle wearer (ocular center of rotation, entrance pupil, and/or principal plane, etc.);
  parameters of a standard position of wear or arrangement of the spectacle lens pair in front of the eyes of the spectacle wearer (face form angle, forward inclination, corneal vertex distance, etc.); and/or parameters of a standard object model or standard object distance.

For example, the position of wear can be specified on the basis of a standardized position of wear. If the spectacle frame or the spectacles according to a standardized position of wear are used, the ocular center of rotation distance is approx. 27.4 mm or approx. 27.9 mm or approx. 28.5 mm or approx. 28.8 mm, the forward inclination, i.e. the pantoscopic angle, is approx. 8°, the face form angle is approx. 0°, the pupillary distance is approx. 63 mm, the corneal vertex distance is approx. 15 mm, the object distance in the distance reference point is approx. 0 D, and the object distance in the near reference point is approx. −2.5 D.

In particular, if the spectacle frame or the spectacles according to a standardized position of wear are used, the ocular center of rotation distance is approx. 26.5 mm, the forward inclination, i.e. the pantoscopic angle, is approx. 9°, the face form angle is approx. 5°, the pupillary distance is approx. 64 mm, and the corneal vertex distance is approx. 13 mm.

Alternatively, if the spectacle frame or the spectacles according to a standardized position of wear are used, the ocular center of rotation distance is approx. 28.5 mm, the forward inclination, i.e. the pantoscopic angle, is approx. 7°, the face form angle is approx. 0°, the pupillary distance is approx. 63 mm, and the corneal vertex distance is approx. 15 mm.

Alternatively, if the spectacle frame or the spectacles according to a standardized position of wear are used, the ocular center of rotation distance is approx. 25 mm, the forward inclination, i.e. the pantoscopic angle, is approx. 8°, the face form angle is approx. 5°, the pupillary distance is approx. 64 mm, and the corneal vertex distance is approx. 13 mm.

Alternatively, if the spectacle frame or the spectacles according to a standardized position of wear are used, the ocular center of rotation distance is approx. 27.5 mm, the forward inclination, i.e. the pantoscopic angle, is approx. 11°, the face form angle is approx. 0°, the pupillary distance is approx. 65 mm, and the corneal vertex distance is approx. 14 mm.

The following numerical parameters e.g. characterize an average situation of wear:
 corneal vertex distance (CVD)=15.00 mm;
 pantoscopic angle=8.0 degrees;
 face form angle=0.0 degrees;
 pupillary distance=63.0 mm;
 ocular center of rotation distance e=28.5 mm;
 object distance model: infinite object distance in the upper portion of the spectacle lens, which smoothly transitions to an object distance of 2.6 D with x=0 mm, y=−20 mm.

Alternatively, individual parameters of the eye or the eyes of a specific spectacle wearer (ocular center of rotation, entrance pupil, and/or principal plane, etc.), the individual position of wear or arrangement in front of the eyes of the spectacle wearer (face form angle, pantoscopic angle, corneal vertex distance, etc.), and/or the individual object distance model can be taken into consideration.

For oblique or diagonal directions of sight of the first or the second eye, a fixed, tilted coordinate system is described, in which the wavefront is illustrated and which is appropriately associated with the base coordinate system in the straight direction of sight, to which system the refraction data preferably refer.

Preferably, this coordinate transition is appropriately described e.g. by Helmholtz coordinates $(\phi, \vartheta, \psi)$. In other preferred embodiments, a different representation, such as Fick's coordinates or Euler angle, could be used. In the following, a preferred use of the Helmholtz coordinates is exemplarily described. This may be performed separately for each eye, which is expressed by a superscript "(1)" for the first eye or "(2)" for the second eye, or in some examples also by a superscript "(l)" for the left eye or "(r)" for the right eye. As far as it is not explicitly distinguished between the first and the second eye, this index may be omitted for the sake of simplicity.

Thus, determining the primary direction of sight $-e_{\zeta}^{(1,p)}$ of the first eye preferably comprises determining a primary first Helmholtz angle $\vartheta^{(1,p)}$ of the first eye and a primary second Helmholtz angle $\phi^{(1,p)}$ of the first eye for the at least one first primary evaluation point $i_b^{(1,p)}$ of the first spectacle lens such that the reference direction of sight $-e_z^{(1)}$ of the first eye transitions into the primary direction of sight $-e_{\zeta}^{(1,p)}$ of the first eye by a combination of a first rotation of the first eye about a horizontal first rotation axis $e_x^{(1)}$ of the first eye, which is perpendicular to the reference direction of sight $-e_z^{(1)}$ of the first eye, (in particular through the ocular center of rotation) of the first eye (first base axis of the first eye) by the primary first Helmholtz angle $\vartheta^{(1,p)}$ of the first eye, and of a second rotation of the first eye about a primary second rotation axis $e_{y,H}^{(1,p)}$ of the first eye by the primary second Helmholtz angle $\phi^{(1,p)}$ of the first eye, wherein the primary second rotation axis $e_{y,H}^{(1)}$ of the first eye is an axis that is rotated about the first rotation axis $e_x^{(1)}$ of the first eye by the primary first Helmholtz angle $\vartheta^{(1,p)}$ of the first eye with respect to an axis $e_y^{(1)}$ (in particular through the ocular center of rotation; second base axis of the first eye), which is perpendicular to the reference direction of sight $-e_z^{(1)}$ of the first eye and to the first rotating axis $e_x^{(1)}$ of the first eye.

Preferably, determining the corresponding primary direction of sight $-e_{\zeta,k}^{(2,p)}$ of the second eye comprises determining a corresponding primary first Helmholtz angle $\vartheta_{,k}^{(2,p)}$ of the second eye and a corresponding primary second Helmholtz angle $\phi_k^{(2,p)}$ of the second eye (in particular with respect to a reference direction of sight $-e_z^{(2)}$ of the second eye) such that the reference direction of sight $-e_z^{(2)}$ of the second eye transitions into the corresponding primary direction of sight $-e_{\zeta,k}^{(2,p)}$ of the second eye by a combination of a first rotation of the second eye about a horizontal first rotation axis $e_x^{(2)}$ of the second eye, which is perpendicular to the reference direction of sight $-e_z^{(2)}$ (in particular through the ocular center of rotation) of the second eye (first base axis of the second eye), by the corresponding primary first Helmholtz angle $\vartheta_{,k}^{(2,p)}$ of the second eye, and of a second rotation of the second eye about a corresponding primary second rotation axis $e_{y,H,k}^{(2,p)}$ of the second eye by the corresponding primary second Helmholtz angle $\phi_k^{(2,p)}$ of the second eye, wherein the corresponding primary second rotation axis $e_{y,H,k}^{(2,p)}$ of the second eye is an axis that is rotated about the first rotation axis $e_x^{(2)}$ of the second eye by the corresponding primary first Helmholtz angle $\vartheta_{,k}^{(2,p)}$ of the second eye with respect to an axis $e_y^{(2)}$ (in particular through the ocular center of rotation; second base axis of the second eye), which is perpendicular to the reference direction of sight $-e_z^{(2)}$ of the second eye and to the first rotating axis $e_x^{(2)}$ of the second eye.

The determination of Helmholtz angles described for the primary direction of sight of the first eye and the corresponding primary direction of sight of the second eye can analogously also be applied to primary directions of sight of the second eye as well as to secondary, tertiary, etc., directions of sight of the first and/or the second eye and to the corresponding directions of sight. Thus, determining a direction of sight $-e_{\zeta}^{(i)}$ or $-e_{\zeta,k}^{(i)}$ of an eye, in particular of the first (i=1) and/or the second (i=2) eye, preferably comprises determining a first Helmholtz angle $\vartheta^{(i)}$ of the eye and a second Helmholtz angle $\phi^{(i)}$ of the eye. These angles are particularly determined such that the reference direction of sight $-e_z^{(i)}$ of the eye transitions into the corresponding direction of sight $-e_\zeta^{(i)}$ or $-e_{\zeta,k}^{(i)}$ of the eye by a combination of

- a first rotation of the eye about a first rotating axis $e_x^{(i)}$ (first base axis of the eye) by the first Helmholtz angle $\vartheta,^{(i)}$, and
- a second rotation of the eye about a second rotating axis $e_{y,H}^{(i)}$ by the second Helmholtz angle $\phi^{(i)}$.

Here, the first rotating axis $e_x^{(i)}$ is perpendicular to the reference direction of sight $-e_z^{(i)}$ of the eye and, in the specific situation of wear (in particular for the usual straight head posture of the spectacle wearer), runs horizontally through the ocular center of rotation of the eye. The second rotating axis $e_{y,H}^{(i)}$ of the eye is specified as an axis that results from a second base axis $e_y^{(i)}$ of the eye by a rotation about the first rotating axis $e_x^{(i)}$ of the eye by the first Helmholtz angle $\vartheta,^{(i)}$ of the eye, i.e. that the second base axis $e_y^{(i)}$, which is rotated about the first rotating axis $e_x^{(i)}$ of the eye by the first Helmholtz angle $\vartheta,^{(i)}$ of the eye, coincides with the second rotating axis $e_{y,H}^{(i)}$. The second base axis $e_y^{(i)}$ of the eye in turn is perpendicular both to the reference direction of sight $-e_z^{(i)}$ of the eye and to the first rotating axis $e_x^{(i)}$ of the eye.

Preferably, in addition to the stationary base coordinate system $(e_x, e_y, e_z)$, an ocularly fixed coordinate system or a moving trihedron $(e_{x,H}^{(i)}, e_{y,H}^{(i)}, e_{z,H}^{(i)})$ is defined, which arises from the basis vectors of the base coordinate system when the Helmholtz matrix H is applied:

$$e_{x,H} = H(\vartheta, \varphi, \psi) \cdot e_x \quad (1)$$
$$e_{y,H} = H(\vartheta, \varphi, \psi) \cdot e_y$$
$$e_{z,H} = H(\vartheta, \varphi, \psi) \cdot e_z$$

with $H(\vartheta, \varphi, \psi) := H_x(\vartheta) H_y(-\varphi) H_z(\psi)$ wherein (2)

$$H_x(\vartheta) := \begin{pmatrix} 1 & 0 & 0 \\ 0 & \cos\vartheta & -\sin\vartheta \\ 0 & \sin\vartheta & \cos\vartheta \end{pmatrix} \quad (3)$$

$$H_y(\varphi) := \begin{pmatrix} \cos\varphi & 0 & \sin\varphi \\ 0 & 1 & 0 \\ -\sin\varphi & 0 & \cos\varphi \end{pmatrix}$$

$$H_z(\vartheta) := \begin{pmatrix} \cos\psi & -\sin\psi & 0 \\ \sin\psi & \cos\psi & 0 \\ 0 & 0 & 1 \end{pmatrix}$$

The angles $\phi$ and $\vartheta$ specify the direction of sight, while the angle $\psi$ describes the torsion adjustment of the eye. The vector $HS = e_\zeta^{(i)}$ (i=1,2) indicates the vector of the eye-side main ray for the first (i=1) or the second eye (i=2) in the definition of the moving trihedron. Since it is fixedly coupled to the direction of sight, the two viewing angles $\phi$ and $\vartheta$, can be reconstructed from the vector HS according to $$\varphi = -\arcsin HS_x, \quad -\frac{\pi}{2} < \varphi < \frac{\pi}{2} \quad (4)$$

$$\vartheta = -\arctan\frac{HS_y}{HS_z}, \quad -\frac{\pi}{2} < \vartheta < \frac{\pi}{2}$$

The third angle $\psi$, however, cannot be derived from the direction of sight, but instead arises from an appropriate torsion adjustment of the eye. For this, different physiological models are available. For example, a model demanding that the final position of the eye is specified in that the eye is brought to the final position by a rotation about the torsion reference axis $e_L$ from the zero direction of sight, wherein the torsion reference axis $e_L$ is characterized in that it entirely lies in the plane that is perpendicular to the zero direction of sight, is referred to as Listing's model or Listing's rule "L1" or Listing's rule for distance vision, since it only provides a good approximation for distance vision. In particular, the torsion reference axis $e_L$ in Helmholtz coordinates is given by $$e_L = \frac{1}{1 + \tan\frac{\varphi}{2}\tan\frac{\vartheta}{2}\tan\frac{\psi}{2}} \begin{pmatrix} \tan\frac{\vartheta}{2} - \tan\frac{\psi}{2}\tan\frac{\varphi}{2} \\ -\tan\frac{\varphi}{2} - \tan\frac{\vartheta}{2}\tan\frac{\psi}{2} \\ \tan\frac{\psi}{2} - \tan\frac{\varphi}{2}\tan\frac{\vartheta}{2} \end{pmatrix} \quad (5)$$

wherein the last component of the axis $e_L$ disappears. i.e.

$$\tan\frac{\psi}{2} - \tan\frac{\varphi}{2}\tan\frac{\vartheta}{2} = 0 \Leftrightarrow \psi_{Helmholtz}(\varphi, \vartheta) \quad (6)$$

$$= 2\arctan\left(\tan\frac{\varphi}{2}\tan\frac{\vartheta}{2}\right)$$

i.e. the torsion angle $\psi$ can be seen as a function of the viewing angles according to Listing's rule L1.

Preferably, the first primary torsion correction angle $\psi_\Delta^{(1,p)}(e_\zeta^{(1,p)}, e_{\zeta,k}^{(2,p)})$ depends both on the determined primary direction of sight $-e_\zeta^{(1,p)}$ of the first eye and on the determined corresponding primary direction of sight $-e_{\zeta,k}^{(2,p)}$ of the second eye. Analogously, the second primary torsion correction angle and/or the first and/or the second secondary and/or tertiary, etc., torsion correction angle depends both on the determined direction of sight of the respective eye and on the determined corresponding direction of sight of the respective other eye. In particular, the torsion correction angle preferably depends on the first and second Helmholtz angles of the first and second eyes.

Particularly preferably, it holds for the first torsion correction angle $\psi_\Delta^{(1)}$:

$$\psi_\Delta^{(1)} = \arctan\left(\tan\left(\frac{\vartheta_k^{(2)}}{2}\right)\cdot\tan\left(\frac{\varphi_k^{(2)}}{2}\right)\right) - \arctan\left(\tan\left(\frac{\vartheta^{(1)}}{2}\right)\cdot\tan\left(\frac{\varphi^{(1)}}{2}\right)\right) \quad (7)$$

This value particularly results in the Helmholtz representation from the formation of the mean value from the Helmholtz torsion angles of the first and second eyes:

$$L2: \psi_{corrected}^{(1)} = \psi_{corrected}^{(2)} = \frac{\psi_{Helmholtz}(\varphi^{(1)}, \vartheta^{(1)}) + \psi_{Helmholtz}(\varphi_k^{(2)}, \vartheta_k^{(2)})}{2} \quad (8)$$

Alternatively or in addition, it preferably holds for the second torsion correction angle $\psi_\Delta^{(2)}$ in an analogue manner:

$$\psi_\Delta^{(2)} = \arctan\left(\tan\left(\frac{\vartheta_k^{(1)}}{2}\right)\cdot\tan\left(\frac{\varphi_k^{(1)}}{2}\right)\right) - \arctan\left(\tan\left(\frac{\vartheta^{(2)}}{2}\right)\cdot\tan\left(\frac{\varphi^{(2)}}{2}\right)\right).$$

Thus, a very quick optimization can be achieved with a very good optimization result. In another preferred embodiment, it holds for the first torsion correction angle $\psi_\Delta^{(1)}$:

$$\psi_\Delta^{(1)} = 2 \cdot \arctan\left(\frac{\tan\left(\frac{\vartheta^{(1)} + \vartheta_k^{(2)}}{4}\right)}{\tan\left(\frac{\varphi^{(1)} + \varphi_k^{(2)}}{4}\right)}\right) - 2 \cdot \arctan\left(\frac{\tan\left(\frac{\vartheta^{(1)}}{2}\right)}{\tan\left(\frac{\varphi^{(1)}}{2}\right)}\right) \qquad (9)$$

Alternatively or in addition, it preferably holds for the second torsion correction angle $\psi_\Delta^{(2)}$ in an analogue manner:

$$\psi_\Delta^{(2)} = 2 \cdot \arctan\left(\frac{\tan\left(\frac{\vartheta^{(2)} + \vartheta_k^{(1)}}{4}\right)}{\tan\left(\frac{\varphi^{(2)} + \varphi_k^{(1)}}{4}\right)}\right) - 2 \cdot \arctan\left(\frac{\tan\left(\frac{\vartheta^{(2)}}{2}\right)}{\tan\left(\frac{\varphi^{(2)}}{2}\right)}\right)$$

This value represents a further simplification and acceleration of the calculation and offers a very good approximation of equation (8). For different vertical prism differences, the results of the formulae (8) and (9) differ from the common Listing's Rule L1 by maximally 0.2° or by maximally 2% of the absolute value of the torsion correction if viewing angles of up to 50° are taken into consideration. If the vertical prism difference is not greater than 3 cm/m, the approximation error of equation (9) with respect to equation (8) is maximally 0.4°, but only for extreme viewing angles.

Equation (9) arises particularly from the cyclopean eye model by averaging Helmholtz angles according to $$\varphi^{(Z)} = \frac{\varphi + \varphi_k}{2},$$
$$\vartheta^{(Z)} = \frac{\vartheta + \vartheta_k}{2}$$

And evaluation of equation (8) for the mean values:

$$L2: \psi_{corrected}^{(1)} = \psi_{corrected}^{(2)} \approx \psi_{Helmholtz}(\varphi^{(z)}, \vartheta^{(z)})$$

The described modifications of Listing's Rule L1 for distance vision will be referred to as Listing's Rule L2 for near vision in the following.

Thus, spectacle lenses can be optimized without a great technical effort, since the Helmholtz torsions can be calculated in a simple manner. Moreover, the exemplary embodiments can be applied without restrictions to the vertical viewing angles for left and right.

In a preferred embodiment, during a calculation or optimization step of one spectacle lens, the other lens remains unchanged. In the evaluation of the merit function for each point or each evaluation point in the merit function of a lens, the corresponding visual point of the lens, which remains unchanged, is calculated, so that the Helmholtz angles can be determined therefrom. For the calculation of the deviation between desired and actual values of the astigmatism in the merit function, the torsional position of the eye is preferably determined according to equations (8) and (9).

Preferably, the method comprises providing a first or a second starting surface, respectively, for the at least one surface of the first and/or the second spectacle lens, wherein the starting surface is determined by minimizing a monocular merit function, which does not depend on the corresponding direction of sight $-e_{\zeta,k}$ of the other eye. In a preferred embodiment, the torsion correction angle is equal to zero. In another preferred embodiment, the Helmholtz torsion is equal to zero.

Preferably, the method comprises specifying at least one torsion correction area, in particular a first and/or a second torsion correction area, of the first or second spectacle lens, respectively, in particular of the spectacle lens pair to be optimized and produced, which area comprises a multitude of first or second evaluation points $i_b$, respectively, of the respective spectacle lens, wherein the determination of the first or second direction of sight $-e_\zeta$, respectively, is performed for each evaluation point i of the first or second spectacle lens, respectively, and the determination of the corresponding direction of sight $-e_{\zeta,k}$ of the respective other eye is performed at least for each evaluation point $i_b$ of the corresponding torsion correction area, and wherein in the merit function, for at least each evaluation point $i_b$ or the corresponding torsion correction area, a correction of a respective transformed astigmatic refraction by the respective spectacle lens in the specific situation of wear is taken into account such that the respective torsion correction angle $\psi_\Delta(e_{\zeta,k})$ depends on the determined corresponding direction of sight $-e_{\zeta,k}$.

Preferably, the torsion correction area of the first and/or the second spectacle lens comprises a near zone of the spectacle lens at least in parts. Particularly preferably, the torsion correction area comprises a near reference point of the spectacle lens. The torsion correction area preferably does not comprise a distance zone of the spectacle lens at least in parts. In a preferred embodiment, in the merit function for each evaluation point i of the spectacle lens not comprised by the torsion correction area, a correction of a transformed astigmatic refraction by the spectacle lens in the specific situation of wear is taken into account such that the correction torsion angle $\psi_K$ matches with the respective reference torsion angle $\psi_0$. In this embodiment, the optimization is performed outside the specified torsion correction area on the basis of Listing's rule, according to which the corresponding direction of sight does in particular not have to be taken into account. This is of particular advantage in a distance portion or distance zone of the spectacle lens or the spectacle lens pair, where the influence of the direction of sight of the second eye on the torsional position of the first eye is little. Despite the fact that a good correction quality of the spectacle lens pair is obtained, the optimization and production can be performed in a quick and efficient manner, since the computing effort is kept low. Here, the merit function for evaluation points outside the torsion correction area and in particular at least partially for evaluation points of the distance zone does not depend on the corresponding direction of sight of the other eye. This simplifies the calculation or optimization step(s) and leads to a faster optimization and production of the spectacle lens pair. In particular, for very remote object points, the influence of the second eye on the torsion of the first eye for the fusion of the images for binocular vision is less great than for object points that are near or not that far away, which is why a binocular torsion correction is omitted preferably at least partially in the distance zone in favor of a faster optimization and production of the spectacle lens pair.

In particular, the disclosure herein relates to a method for optimizing and producing a spectacle lens pair or a spectacle lens for a pair of spectacle lenses for correcting anisometropia. In particular in the correction of anisometropia, significant prismatic differences often occur between the right and left spectacle lenses especially in the case of a non-central direction of sight, which has a significant influence on the convergence movement of the eyes and thus on the torsional position in the respective evaluation point for these directions of sight or the corresponding evaluation points. According to the embodiments disclosed herein, a significant improvement of the imaging quality can be achieved in particular for such types of spectacles.

Preferably, the corresponding direction of sight $-e_{\zeta,k}$, which corresponds to the first and/or the second direction of sight $-e_\zeta$ in the specific situation of wear, is determined for the at least one evaluation point $i_b$ of the first and/or the second spectacle lens by ray tracing assuming orthotropia.

Moreover, the disclosure herein relates to a use of a spectacle lens or a spectacle lens pair, produced according to one of the above-described methods, in spectacles for correcting anisometropia.

Furthermore, the disclosure herein provides a computer program product including program parts, which, when loaded and executed on a computer, are adapted to perform a method for optimizing at least a first spectacle lens for a specific situation of wear for correcting at least a first astigmatic refraction of a first eye of a spectacle wearer, which has a first cylinder reference axis $\alpha_0^{(1)}$ in a reference direction of sight $-e_z^{(1)}$ of the first eye, wherein the method comprises at least a first primary calculation or optimization step of the first spectacle lens, which comprises:

determining a primary direction of sight $-e_\zeta^{(1,p)}$ of the first eye for at least one primary evaluation point $i_b^{(1,p)}$ of the first spectacle lens;

determining a corresponding primary direction of sight $-e_{\zeta,k}^{(2,p)}$ of a second eye of the spectacle wearer, which corresponds to the primary direction of sight $-e_\zeta^{(1,p)}$ of the first eye in the specific situation of wear, in particular depending on starting values for a second spectacle lens, which is particularly intended to be used with the first spectacle lens in a spectacle lens pair; and minimizing a first primary merit function for at least one surface of the first spectacle lens, wherein in the first primary merit function for the at least one primary evaluation point $i_b^{(1,p)}$ of the first spectacle lens, a correction of a first primary transformed astigmatic refraction by the first spectacle lens in the specific situation of wear is taken into account such that the first primary transformed astigmatic refraction depends on the determined corresponding primary direction of sight $-e_{\zeta,k}^{(2,p)}$ of the second eye.

Preferably, the computer program product comprises program parts, which, when loaded and executed on a computer, are adapted to perform a method according to the present exemplary embodiments thereof.

Furthermore, the disclosure herein provides a storage medium with a computer program stored thereon, said computer program being adapted, when loaded and executed on a computer, to perform a method for optimizing at least a first spectacle lens for a specific situation of wear for correcting at least a first astigmatic refraction of a first eye of a spectacle wearer, which has a first cylinder reference axis $\alpha_0^{(1)}$ in a reference direction of sight $-e_z^{(1)}$ of the first eye, wherein the method comprises at least a first primary calculation or optimization step of the first spectacle lens, which comprises:

determining a primary direction of sight $-e_\zeta^{(1,p)}$ of the first eye for at least one primary evaluation point $i_b^{(1,p)}$ of the first spectacle lens;

determining a corresponding primary direction of sight $-e_{\zeta,k}^{(2,p)}$ of a second eye of the spectacle wearer, which corresponds to the primary direction of sight $-e_\zeta^{(1,p)}$ of the first eye in the specific situation of wear, in particular depending on starting values for a second spectacle lens, which is particularly intended to be used with the first spectacle lens in a spectacle lens pair; and minimizing a first primary merit function for at least one surface of the first spectacle lens, wherein in the first primary merit function for the at least one primary evaluation point $i_b^{(1,p)}$ of the first spectacle lens, a correction of a first primary transformed astigmatic refraction by the first spectacle lens in the specific situation of wear is taken into account such that the first primary transformed astigmatic refraction depends on the determined corresponding primary direction of sight $-e_{\zeta,k}^{(2,p)}$ of the second eye.

Preferably, a computer program code is stored on the storage medium, which, when loaded and executed on a computer, is adapted to perform a method according to the exemplary embodiments thereof.

Finally, the disclosure herein provides an apparatus for producing at least a first spectacle lens, in particular a spectacle lens pair, wherein the apparatus comprises gathering means or a gathering unit for gathering merit data of a spectacle lens pair and calculation and optimization means or a calculation and optimization unit for calculating and optimizing at least a first spectacle lens. In particular, the gathering unit or the gathering means is/are adapted to gather prescription data, such as a first astigmatic refraction of a first eye of a spectacle wearer, which in a first reference direction of sight $-e_z^{(1)}$ of the first eye has a first cylinder value and a first cylinder reference axis $\alpha_0^{(1)}$, and/or a second astigmatic refraction of a second eye of the spectacle wearer, which in a reference direction of sight $-e_z^{(2)}$ of the second eye has a second cylinder value and a second cylinder reference axis $\alpha_0^{(2)}$. Preferably, the gathering means are further adapted to at least partially gather or specify the specific situation of wear.

The calculation and optimization means are adapted to calculate and optimize at least a first spectacle lens for a specific situation of wear for correcting at least the first astigmatic refraction of the first eye of the spectacle wearer, wherein the calculation and optimization are performed such as to comprise at least a first primary calculation or optimization step of the first spectacle lens, which comprises:

determining a primary direction of sight $-e_\zeta^{(1,p)}$ of the first eye for at least one primary evaluation point $i_b^{(1,p)}$ of the first spectacle lens;

determining a corresponding primary direction of sight $-e_{\zeta,k}^{(2,p)}$ of a second eye of the spectacle wearer, which corresponds to the primary direction of sight $-e_\zeta^{(1,p)}$ of the first eye in the specific situation of wear, in particular depending on starting values for a second spectacle lens, which is particularly intended to be used with the first spectacle lens in a spectacle lens pair; and minimizing a first primary merit function for at least one surface of the first spectacle lens, wherein in the first primary merit function for the at least one primary evaluation point $i_b^{(1,p)}$ of the first spectacle lens, a correction of a first primary transformed astigmatic refraction by the first spectacle lens in the specific situation of wear is taken into account such that the first primary transformed astigmatic refraction depends on the determined corresponding primary direction of sight $-e_{\zeta,k}^{(2,p)}$ of the second eye.

Preferably, the apparatus is adapted to perform a method according to the exemplary embodiment thereof.

As the merit function, in particular as the first and/or the second primary and/or secondary merit function, in particular a function F with the following functional relationship to the spherical power S, the amount of the cylindrical power Z, and the axial position of the cylinder a (also referred to as a "SZA" combination) is taken into account and minimized:

$$F = \sum_{i=1}^{m} [g_{i,s\Delta}(s_{\Delta,i} - s_{\Delta,i,desired})^2 + g_{i,Z\Delta}(Z_{\Delta,i} - Z_{\Delta,i,desired})^2 + \ldots].$$

Here, at least the actual refraction deficits of the spherical power $S_{\Delta,i}$ and the cylindrical power $Z_{\Delta,i}$ as well as desired values for the refraction deficits of the spherical power $S_{\Delta,i,desired}$ and the cylindrical power $Z_{\Delta,i,desired}$ are taken into account in the merit function F at the evaluation points i of the respective spectacle lens. The respective refraction deficits at the respective evaluation points are preferably taken into account with weighting factors $g_{i,S\Delta}$ or $g_{i,Z\Delta}$. Here, the desired values for the refraction deficits of the spherical power $S_{\Delta,i,desired}$ and/or the cylindrical power $Z_{\Delta,i,desired}$ particularly together with the weighting factors $g_{i,S\Delta}$ or $g_{i,Z\Delta}$ form the so-called spectacle lens design. In addition, particularly further residues, in particular further variables to be optimized, such as coma and/or spherical aberration and/or prism and/or magnification and/or anamorphotic distortion, etc., can be taken into account, which is in particular implied by the expression "+ . . .".

If, in spectacle lens calculation, one considers the ray tracing through a specific visual point i, i.e. a spectacle lens evaluation point of the respective spectacle lens, then the wavefront has a specific SZA combination at the vertex sphere. The aim of the spectacle lens optimization is for this SZA combination to match with the SZA combination of the refraction determination or, in conformity with the exemplary embodiments, with a transformed SZA combination depending on the respective direction of sight in the best possible way. Since, as a rule, this is not achieved simultaneously at all visual points i at the same time, a merit function is established, the minimization of which leads to a most suitable compromise with respect to all evaluation points or visual points i.

A preferred basic approach is for example described in Diepes H., Blendowske R. "Optik and Technik der Brille", Optische Fachveröffentlichung GmbH, Heidelberg (2002), in particular on pages 481 ff. To this end, the so-called refractive power matrix or vergence matrix S is considered, which is related to the values for the spherical power S, the amount of the cylindrical power Z, and the axial position of the cylinder α as follows:

$$S = \begin{pmatrix} S_{xx} & S_{xy} \\ S_{xy} & S_{yy} \end{pmatrix}$$

$$= \begin{pmatrix} \left(S + \frac{Z}{2}\right) - \frac{Z}{2}\cos 2\alpha & -\frac{Z}{2}\sin 2\alpha \\ -\frac{Z}{2}\sin 2\alpha & \left(S + \frac{Z}{2}\right) + \frac{Z}{2}\cos 2\alpha \end{pmatrix}$$

$$Z = \sqrt{(S_{xx} - S_{yy})^2 + 4S_{xy}^2} \Leftrightarrow S = \frac{1}{2}(S_{xx} + S_{yy} - Z)$$

$$\tan\alpha = \frac{S - S_{xx}}{S_{xy}}$$

The vergence matrix S is determined for the SZA values $S_{SK}$, $Z_{SK}$, $\alpha_{SK}$ at the vertex sphere on the one hand, and for the SZA values $S_{Ref}$, $Z_{Ref}$, $\alpha_{Ref}$ transformed according to the exemplary embodiment from the refraction determination for the at least one eye of the spectacle wearer on the other hand.

This results in $S_{SK}$ or $S_{Ref}$. Visually speaking, $S_{SK}$ describes the local power of the spectacle lens so to speak, while $S_{Ref}$ describes the power desired in the ideal case for the spectacle wearer. According to the exemplary embodiment, not the SZA values determined from the refraction determination for the spectacle wearer are directly used for the determination of $S_{ref}$, but the SZA values transformed for the respective direction of sight of the one eye in dependence on the corresponding direction of sight of the other eye, i.e. in particular the transformed astigmatic refraction. The transformation particularly relates to the viewing angle-dependent determination or specification of the angle $\alpha_{Ref}$, which describes the position of the cylinder correction axis in the transformed astigmatic refraction.

For ideal imaging, it should be demanded that $S_{SK}$ and $S_{Ref}$ match, which cannot be fulfilled for all evaluation points of a spectacle lens at the same time though.

Thus, there remains as the difference matrix:

$$S_\Delta = S_{SK} - S_{Ref}$$

$$= \begin{pmatrix} S_{SK,xx} & S_{SK,xy} \\ S_{SK,xy} & S_{SK,yy} \end{pmatrix} - \begin{pmatrix} S_{Ref,xx} & S_{Ref,xy} \\ S_{Ref,xy} & S_{Ref,yy} \end{pmatrix}$$

$$= \begin{pmatrix} S_{SK,xx} - S_{Ref,xx} & S_{SK,xy} - S_{Ref,xy} \\ S_{SK,xy} - S_{Ref,xy} & S_{SK,yy} - S_{Ref,yy} \end{pmatrix}$$

which is usually different from zero. According to the above-illustrated definition of the vergence matrix, the difference matrix $S_\Delta$ is assigned corresponding SZA values as the refraction deficit:

$$Z_\Delta = \sqrt{((S_{SK,xx} - S_{Ref,xx}) - (S_{SK,yy} - S_{Ref,yy}))^2 + 4(S_{SK,xy} - S_{Ref,xy})^2}$$

$$S_\Delta = \frac{1}{2}((S_{SK,xx} - S_{Ref,xx}) + (S_{SK,yy} - S_{Ref,yy}) - Z_\Delta)$$

$$\tan\alpha_\Delta = \frac{S_\Delta - (S_{SK,xx} - S_{Ref,xx})}{S_{SK,xy} - S_{Ref,xy}}$$

Since the blur of the image in particular only depends on $S_\Delta$ and $Z_\Delta$ (but in particular not on $\alpha_\Delta$) in the case of a non-disappearing $S_\Delta$, an optimization is preferably performed only according to $S_\Delta$ and $Z_\Delta$. The axial position of the wavefront and the transformed refraction are well taken into consideration though. Note that if $S_\Delta=0$ and $Z_\Delta=0$, it follows at the same time that $S_{SK}=S_{Ref}$, $Z_{SK}=Z_{Ref}$ and $\alpha_{SK}=\alpha_{Ref}$. It explicitly holds that:

$$Z_\Delta = \sqrt{Z_{SK}^2 + Z_{Ref}^2 - 2Z_{SK}Z_{Ref}\cos(2(\alpha_{SK} - \alpha_{Ref}))}$$

$$S_\Delta = S_{SK} - S_{Ref} + \frac{1}{2}((Z_{SK} - Z_{Ref}) - Z_\Delta)$$

This shows how the axial position is taken into account in the variables $S_\Delta$ and $Z_\Delta$. A change of the axial position by the angle $\delta\alpha_{SK}$ causes that $\cos(2(\alpha_{SK}+\delta\alpha_{SK}-\alpha_{Ref}))$ instead of $\cos(2(\alpha_{SK}-\alpha_{Ref}))$ is under the root. The optimization is performed with the merit function in that preferably at each visual point i, a desired value $S_{\Delta,i,desired}$ and $Z_{\Delta,i,desired}$ is assigned to each of the variables $S_{\Delta,i}$, $Z_{\Delta,i}$, respectively, and the merit function is minimized after that. For further background information for the understanding of the procedure, reference is made to the article by W. Becken, A. Seidemann, H. Altheimer, G. Esser and D. Uttenweiler "Brillengläser im Sport: Optimierung der Abbildungseigenschaften unter physiologischen Aspekten," Z. Med. Phys. 17 (2007), 56-66.

FIG. 1 shows a graphic definition of Helmholtz coordinates for optimizing a spectacle lens or a spectacle lens pair according to a preferred embodiment. Own Helmholtz coordinates could be introduced for each of the two eyes. In FIG. 1, this is shown exemplarily for only one eye. The ocularly fixed trihedron $(e_{x,H}, e_{y,H}, e_{z,H})$ of the eye results from the spatially fixed trihedron $(e_x, e_y, e_z)$ by the following steps:

1. rotation about the x axis by the angle $\vartheta$ (first Helmholtz angle)
2. rotation about the y axis by the angle $-\varphi$ (second Helmholtz angle)
3. rotation about the new z axis by the angle $\psi$ of the torsion.

Preferably, the z axis $e_z$ describes the direction of the eye-side main ray in the reference direction of sight, while the rotated z axis represents the direction of the eye-side main ray in the first or the second direction of sight.

Figure 2A:
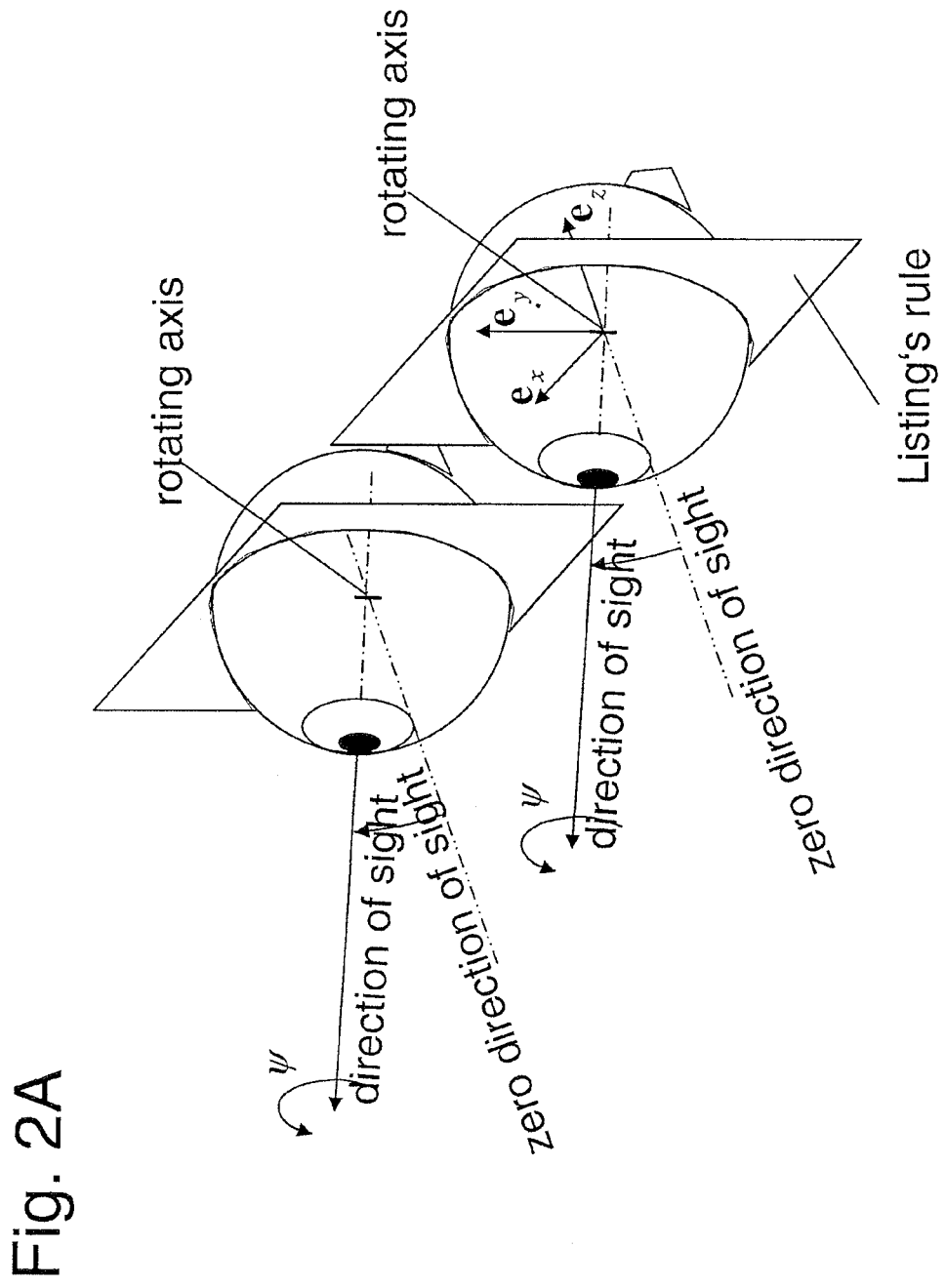
FIG. 2A illustrates an exemplary schematic representation of a pair of eyes with a parallel first and second directions of sight.

FIG. 2A illustrates Listing's rule for distance vision. Both eyes have the same viewing angles $\vartheta$, and $\varphi$, and consequently also the same torsion angle $\psi_{Helmholtz}(\varphi, \vartheta,)$ in the Helmholtz representation according to equation (6). The Helmholtz coordinates relate to the spatially fixed trihedron $(e_x, e_y, e_z)$, which is also drawn in in FIG. 2A.

In particular for some directions of sight, it might be that the torsion angles $\psi^{(l)}$ and $\psi^{(r)}$ in the Helmholtz representation are different for the two eyes, so that the single images do not form on corresponding retina points any more, but on disparate retina points that are twisted to each other. This leads to a binocular double image and fusion disorders. This problem comes up in particular if the eye-side main rays for the lift and right eyes are different. This is either the case for a convergence movement or can be caused by prisms in the lens, which are different for both eyes in the ray path used.

Figure 2B:
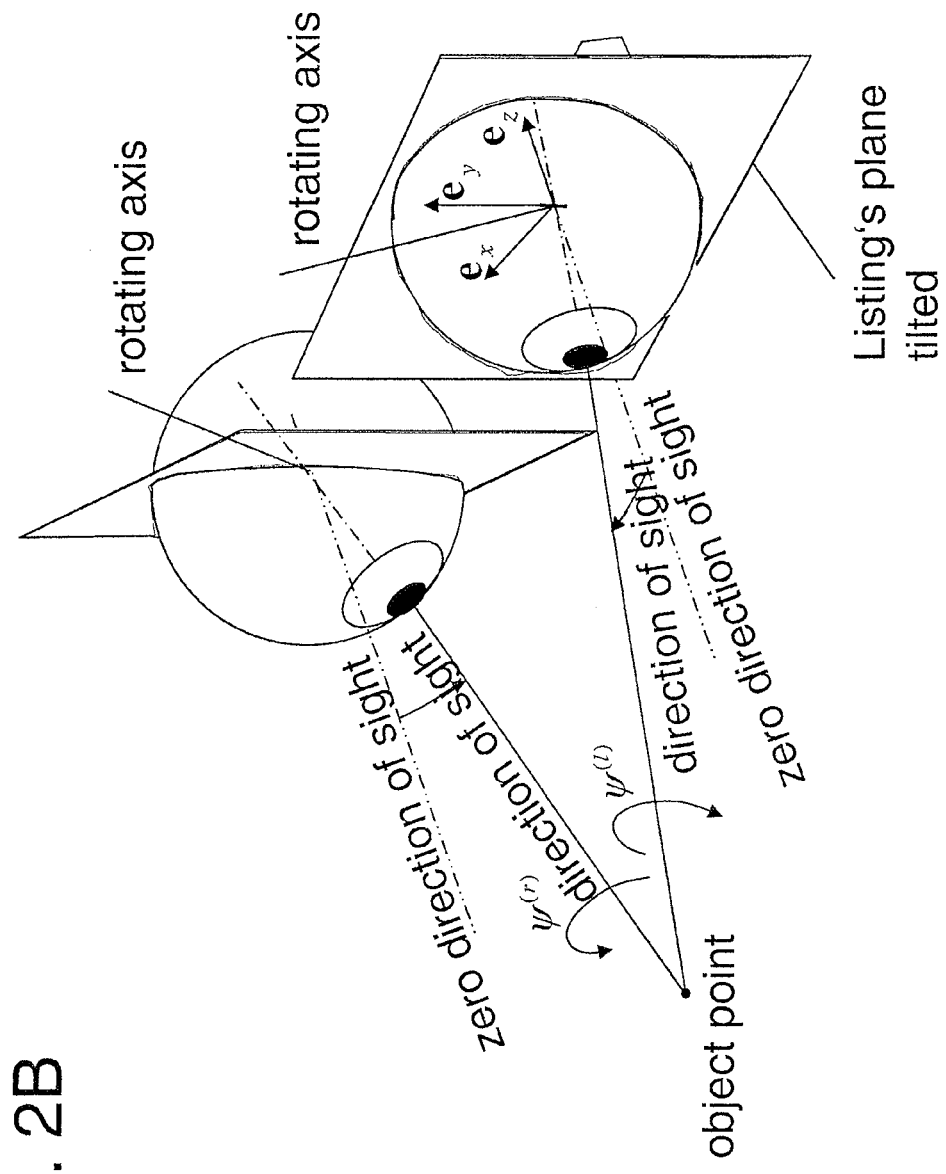
FIG. 2B illustrates an exemplary schematic representation of a pair of eyes with a convergent first and second directions of sight.

In such a case, the torsional movement of the eyes deviates from the specifications of Listing's rule L1, as this is shown in FIG. 2B, for example. FIG. 2B illustrates a modification of Listing's rule according to a preferred embodiment. The eyes converge, and thus the left eye has a different pair of viewing angles $(\varphi^{(l)}, \vartheta,^{(l)})$ than the right eye, which is described by $(\varphi^{(r)}, \vartheta,^{(r)})$. Accordingly, the torsion angles $\psi_{Helmholtz}(\varphi, \vartheta,)$ according to equation (6) are different, $\psi^{(l)} \neq \psi^{(r)}$. The Helmholtz coordinates relate to the spatially fixed trihedron $(e_x, e_y, e_z)$, which is drawn in in FIG. 2B.

The necessity of this torsion correction is also referred to as "Listing's rule for near vision" or "Listing's rule 2 (L2)". The magnitude of this correction is up to 4°, depending on the direction of sight, for a convergence angle of 30° and decreases to zero, as expected, if the convergence angle is almost zero (vision to infinity). According to the disclosure herein, a particularly efficient and flexible optimization of a spectacle lens pair for correcting an astigmatic refraction is provided taking this angle correction into account, which offers great improvement in particular for near vision and for prismatic difference of two spectacle lenses of spectacles.

The following example deals with an object point that lies in the direction of sight oblique to the bottom right with the Helmholtz viewing angles $(\varphi^{(l)}, \vartheta,^{(l)})=(25.0°, -30.0°)$, when viewed from the left eye, and which is to have an object distance $a1^{(l)}=-400.0$ mm (to be measured negatively) from the left ocular center of rotation. To indicate its Cartesian coordinates in the coordinate system shown in FIG. 2B, we will take a look at equation (2) for the left eye (the index "(l)" refers to the coordinates of the left eye). The z axis of the left eye, i.e. $e_{z,H}^{(l)}$, reads in spatially fixed coordinates $$e_{z,H}^{(l)} = H(\vartheta^{(l)}, \varphi^{(l)}, \psi^{(l)}) \cdot e_z \qquad (11)$$

$$= H(\vartheta, \varphi, \psi) \cdot \begin{pmatrix} 0 \\ 0 \\ 1 \end{pmatrix}$$

$$= \begin{pmatrix} -\sin\varphi^{(l)} \\ -\cos\varphi^{(l)}\sin\vartheta^{(l)} \\ \cos\varphi^{(l)}\cos\vartheta^{(l)} \end{pmatrix}$$

$$= \begin{pmatrix} -0.42262 \\ 0.45315 \\ 0.78489 \end{pmatrix},$$

and thus the object point itself is given by $$(x, y, z) = a1^{(l)} e_{z,H}^{(l)} \qquad (12)$$

$$= -400 \text{ mm} \cdot \begin{pmatrix} -0.42262 \\ 0.45315 \\ 0.78489 \end{pmatrix}$$

$$= \begin{pmatrix} 169.05 \\ -181.26 \\ -313.95 \end{pmatrix} \text{ mm}$$

Now, be the right eye remote from the left eye in the distance of the pupillary distance PD=64.0 mm. It can then be calculated that the object point is remote from the right eye by $a1^{(r)}=-377.44$ mm and seen in the direction of the viewing angles $(\varphi^{(r)}, \vartheta,^{(r)})=(16.16°, -30.0°)$, since from the right eye, the object point has the absolute coordinates $$(x, y, z) = PD \cdot e_x + a1^{(r)} e_z^{Auge,(r)} \qquad (13)$$

$$= PD \cdot e_x + a1^{(r)} \begin{pmatrix} -\sin\varphi^{(r)} \\ -\cos\varphi^{(r)}\sin\vartheta^{(r)} \\ \cos\varphi^{(r)}\cos\vartheta^{(r)} \end{pmatrix}$$

$$= 64.0 \text{ mm} \cdot \begin{pmatrix} 1 \\ 0 \\ 0 \end{pmatrix} - 377.44 \text{ mm} \cdot \begin{pmatrix} -0.27832 \\ 0.48024 \\ 0.83181 \end{pmatrix}$$

$$= \begin{pmatrix} 169.05 \\ -181.26 \\ -313.95 \end{pmatrix} \text{ mm},$$

which matches with the point in equation (12) seen from the left eye.

To apply Listing's rule, according to equations (6, 7), one obtains for the two eyes $$\psi^{(l)}=-6.80°, \psi^{(r)}=-4.357°. \qquad (14)$$

Now, Listing's rule for near vision states that instead of the different angles indicated in equation (14), the two eyes assume the mean value of equation (8), i.e.

$$L2: \psi_{corrected}^{(l)} = \psi_{corrected}^{(r)} \qquad (15)$$

$$= \frac{(-6.80°) + (-4.357°)}{2}$$

$$= -5.578°$$

as the torsional position, which is a correction of 1.221° with respect to Listing's rule for distance vision.

In this simplified example, the influences of the spectacle lens e.g. by their local prismatic effects are not shown. In a preferred method, they are taken into account in the determination of the respective directions of sight, in particular in the determination of the corresponding directions of sight, e.g. by a ray tracing method.

Figure 3:
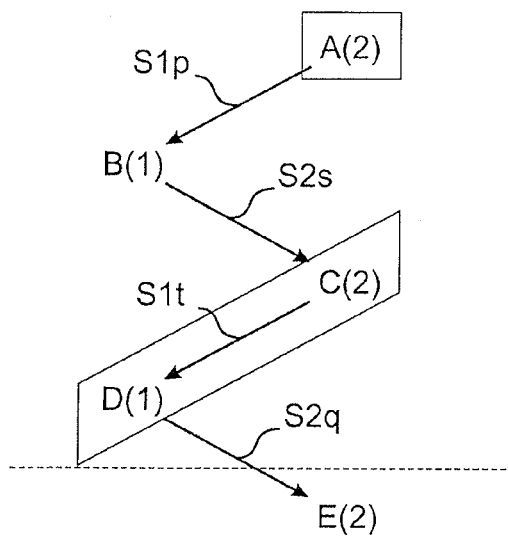
FIG. 3 illustrates an exemplary schematic representation of the course of a method for optimizing and producing a spectacle lens pair according to a first preferred embodiment.

FIG. 3 shows a schematic representation of the course of a method for optimizing and producing a spectacle lens pair according to a first preferred embodiment. Here, a starting lens A(2) in the form of starting values for the second lens, for example the right lens, is taken as a basis. Preferably, this second spectacle lens A(2) is already optimized monocularly for the correction of the eye refraction of the second eye of the spectacle wearer. In a first primary calculation or optimization step S1p, the first spectacle lens is now optimized by minimizing a first primary merit function, while the second spectacle lens A(2) remains unchanged. Thus, in this step S1p, only the parameters or degrees of freedom of the first spectacle lens are varied to obtain a primarily optimized first spectacle lens B(1). The numerical effort can be compared to a conventional monocular optimization. Due to the consideration of the values of the second spectacle lens, in particular the prismatic powers of the second spectacle lens, on the basis of the determination of corresponding directions of sight, a clear improvement of the binocular properties of the spectacle lens pair is achieved though. A monocularly optimized lens might serve as a starting lens for a variation and optimization process of the first spectacle lens in the first primary calculation or optimization step.

In the preferred embodiment illustrated in FIG. 3, a secondarily optimized second spectacle lens C(2) is determined by minimizing a second secondary merit function for the second spectacle lens in a second secondary calculation or optimization step S2s starting from the first spectacle lens B(1) determined in the first primary calculation or optimization step s1p. The primarily optimized first spectacle lens B(1) remains unchanged here. Thus, the numerical effort for the second secondary calculation or optimization step S2s can again be compared to a conventional monocular optimization. The starting value A(2) might serve as the starting lens for a variation or optimization process of the second spectacle lens in the second secondary calculation or optimization step S2s, wherein the lens is varied according to a suitable algorithm until the second secondary merit function has reached the desired convergence.

By analogy, FIG. 3 illustrates as further calculation or optimization steps a first tertiary calculation or optimization step S1t for determining a tertiarily optimized first spectacle lens D(1) depending on the secondarily optimized second spectacle lens C(2), and a second quarternary calculation or optimization step S2q for determining a quarternarily optimized second spectacle lens E(2) depending on the tertiarily optimized first spectacle lens D(1). Preferably, a better binocular optimization of the spectacle lens pair is achieved with an increasing number of these successively performed calculation or optimization steps. Preferably, a termination criterion is defined to thus define as to when the optimization is considered to be sufficiently good. Exemplarily, the optimization is terminated after the first tertiary calculation or optimization step in FIG. 3. The spectacle lens pair [D(1); C(2)], which consists of the tertiarily optimized first spectacle lens D(1) and the secondarily optimized second spectacle lens C(2), is subsequently manufactured or produced for the spectacle wearer.

Figure 4:
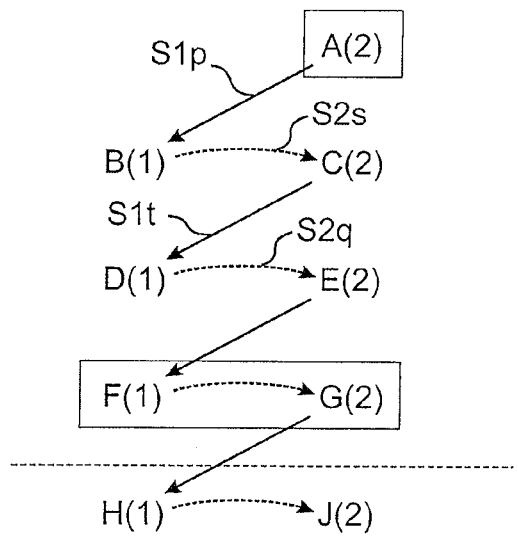
FIG. 4 illustrates an exemplary schematic representation of a method according to a second preferred embodiment.

FIG. 4 shows a schematic representation of a method according to a second preferred embodiment. Here, preferably a first primary calculation or optimization step is performed by analogy with the embodiment shown in FIG. 3. According to the preferred embodiment of FIG. 4, a second secondary calculation or optimization step S2s, however, comprises copying and mirroring the primarily optimized first spectacle lens B(1) to obtain the secondarily optimized second spectacle lens C(2). A subsequent first tertiary calculation or optimization step S1t might again be performed by analogy with the embodiment illustrated in FIG. 3 by minimizing a first tertiary merit function for at least one surface of the first spectacle lens considering the second spectacle lens C(2) obtained by copying and mirroring, in order to obtain a tertiarily optimized first spectacle lens D(1). A subsequent second quarternary calculation or optimization step is again achieved by copying and mirroring. This embodiment of a method is particularly preferred if the prescriptions of the spectacle wearer are symmetric or mirror-symmetric to each other (isometropia). Thereby, a particularly efficient and fast optimization and production of a spectacle lens pair [F(1); G(2)] can be achieved with low computing effort.

Figure 5:
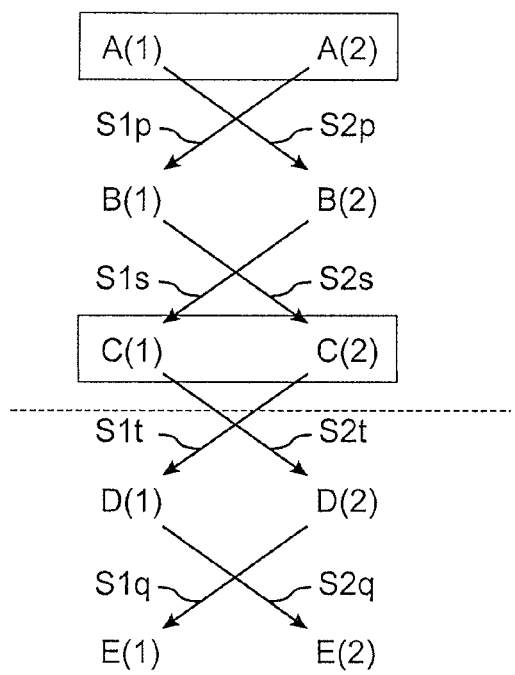
FIG. 5 illustrates an exemplary schematic representation of a method according to a third preferred embodiment.
Figure 6A:
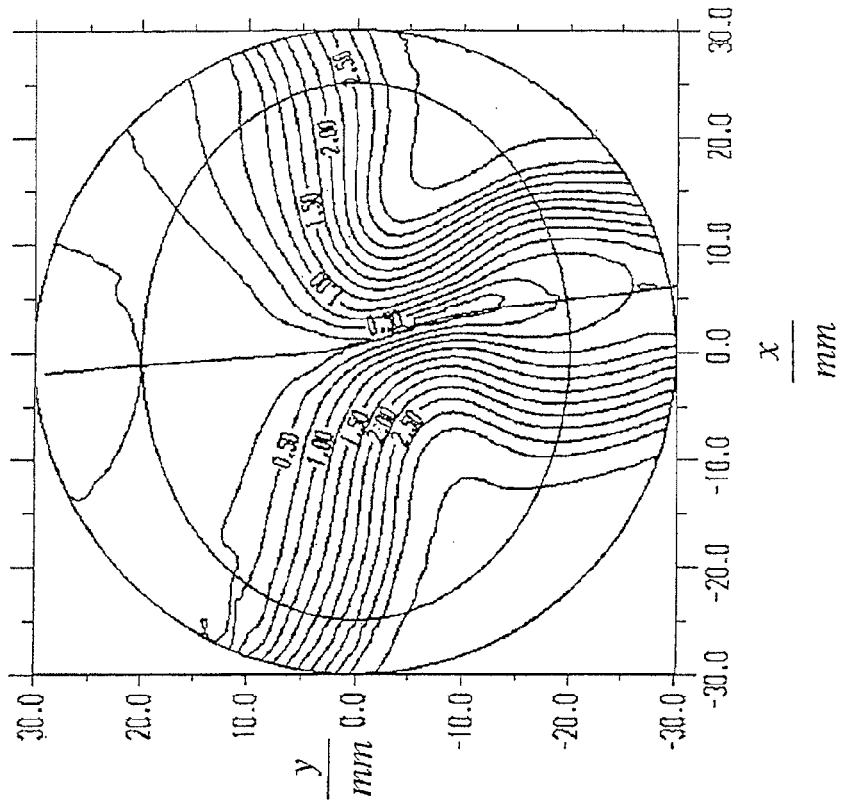
FIG. 6A illustrates exemplary isoastigmatism lines of the refraction deficit of a spectacle lens optimized without considering the direction of sight of the other eye for an evaluation without consideration of the direction of sight of the other eye.
Figure 6B:
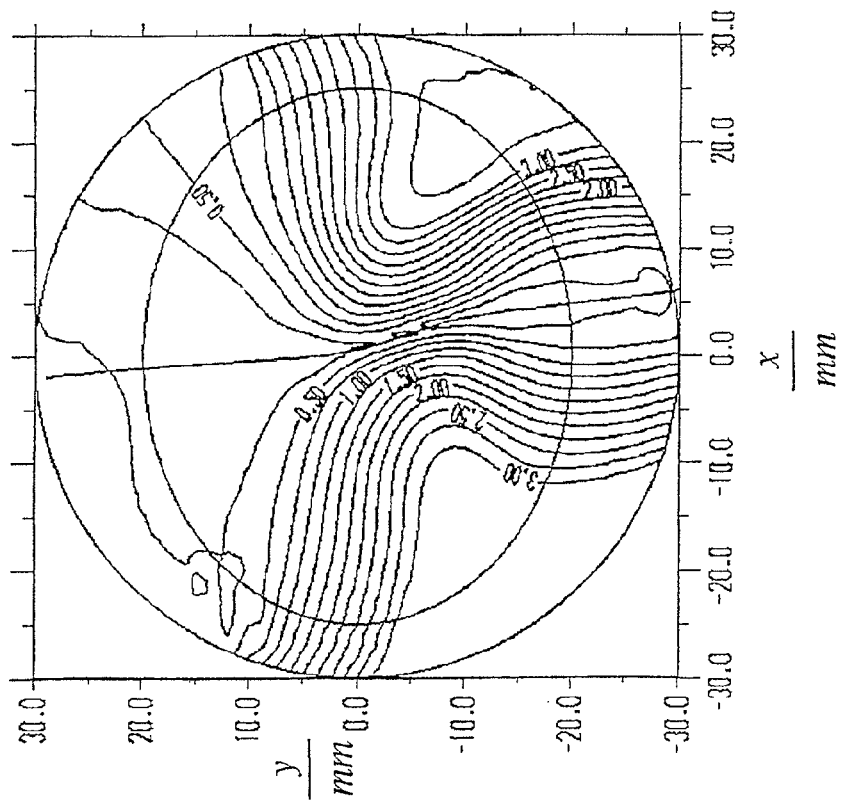
FIG. 6B illustrates exemplary isoastigmatism lines of the refraction deficit of a spectacle lens optimized without considering the direction of sight of the other eye for an evaluation with consideration of the direction of sight of the other eye.
Figure 6D:
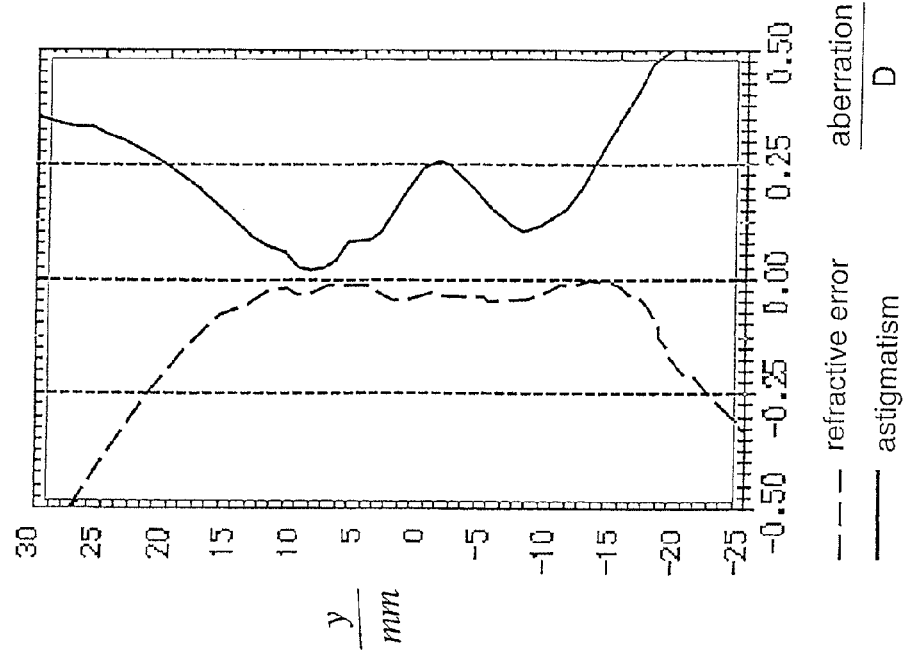
FIG. 6D illustrates an exemplary course of the refraction deficit with respect to the refractive power (left curve) and the astigmatism (right curve) along the main line of FIG. 6B.
Figure 6C:
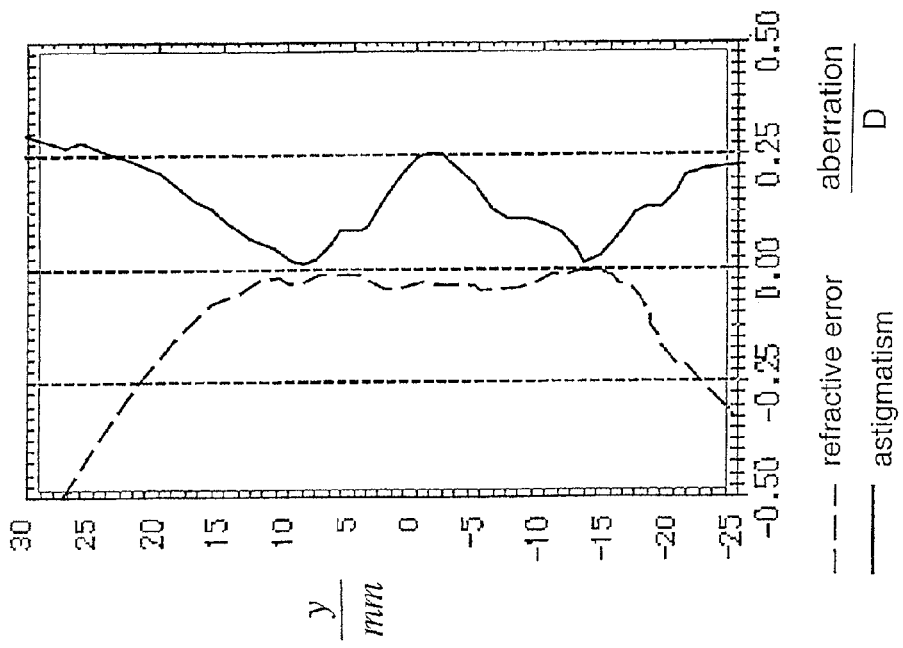
FIG. 6C illustrates an exemplary course of the refraction deficit with respect to the refractive power (left curve) and the astigmatism (right curve) along the main line of FIG. 6A.

FIG. 5 shows a schematic representation of a method according to a third preferred embodiment. Here, preferably in addition to a starting lens A(2) in the form of starting values for the second lens, also a starting lens A(1) in the form of starting values for the first lens is provided. Preferably, this first spectacle lens A(1) is already optimized monocularly for the correction of the eye refraction of the first eye of the spectacle wearer. By analogy and possibly even simultaneously with the first primary calculation or optimization step S1p, as has been described with respect to FIG. 3, the preferred method shown here comprises a second primary calculation or optimization step S2p in which the second spectacle lens is optimized by minimizing a second primary merit function, while the first spectacle lens A(1) remains unchanged. Thus, in this step S2p, only the parameters or degrees of freedom of the second spectacle lens are varied to obtain a primarily optimized first spectacle lens B(1). The lens A(2) might serve as a starting point or starting lens for a variation or optimization process of the second spectacle lens in the second primary calculation or optimization step S2p. Accordingly, the lens A(1) might serve as a starting point or starting lens for a variation or optimization process of the first spectacle lens in the first primary calculation or optimization step S1p.

A secondarily optimized first spectacle lens C(1) is determined by minimizing a first secondary merit function for the first spectacle lens in a first secondary calculation or optimization step S1s starting from the second spectacle lens B(2) determined in the second primary calculation or optimization step S2p. The primarily optimized second spectacle lens B(2) remains unchanged here. By analogy, further first or second tertiary, quarternarily, etc. calculation or optimization steps can be performed until the respective calculation or optimization results D(1), D(2), E(1), E(2), etc. have reached a sufficient convergence. In an exemplary, preferred embodiment of FIG. 5, the iteration is terminated after the determination of the spectacle lens pair [C(1); C(2)], and this spectacle lens pair is manufactured or produced for the spectacle wearer.

Now, in FIG. 6 and FIG. 7, two different spectacle lenses are compared, wherein the first one (FIG. 6, FIG. 7A, FIG. 7C) has been optimized according to Listing's rule L1, and the second one (FIG. 7B, FIG. 7D) constitutes a result of a first primary calculation or optimization step of a method according to a preferred embodiment considering Listing's rule L2. For the optimization and production of the shown lenses, sph=2.0 D, cyl=4.0 D, A30° (axial position=30°), add=3.0 (addition), pr=0,0 (prism) are indicated as prescription values. In particular if a high cylinder and a high addition (and thus a high convergence angle) are chosen, the effects of a torsion correction are particularly striking. If one considers a dependence of the torsional position of the one eye on the direction of sight of the other eye in the description of the physiological reality, the following comparisons result:

a) Change of model for the assessment: One and the same L1-optimized lens is taken. However, it is viewed and assessed with the model L1 (FIGS. 6A, 6C) on the one hand, and with the model L2 (FIGS. 6B, 6D) on the other hand. The result is that the L1-optimized lens assessed with L2 looks slightly worse, i.e. has higher astigmatism values, than if it were assessed with L2.

b) Change of model for the optimization: The two abovementioned different L1 and L2-optimized lenses are considered now. For the assessment, however, the model L2 (FIGS. 6B, 6D, 7B, 7D) assumed to be appropriate is used in both cases.

In FIG. 6, the comparison a) is shown, at the top left there is shown the common astigmatism assessment that comes up for an L2-optimized lens if L1 really reflects the physiology in a realistic manner. At the bottom left there is shown the associated course of the refractive power and the astigmatism on the main line. However, if alternatively the physiological reality is reflected by L2, then the same lens looks completely different (see FIGS. 6B and 6D), i.e. the stronger, the stronger the convergence is. Since it particularly increases in the near portion, the cylinder deficit becomes particularly large there due to the inappropriate axial position, and, accordingly, the near portion would be much narrower than one might think according to L1. The increase of the cylinder deficit with an increasing infraduction can be seen particularly well along the main line, whereas the course of the mean refractive value remains unchanged with respect to the L1-consideration (this is of course exactly expected, since for one and the same lens a changed relative axial position of the crossed cylinders of lens and eye does not influence the mean refractive value).

Figure 7A:
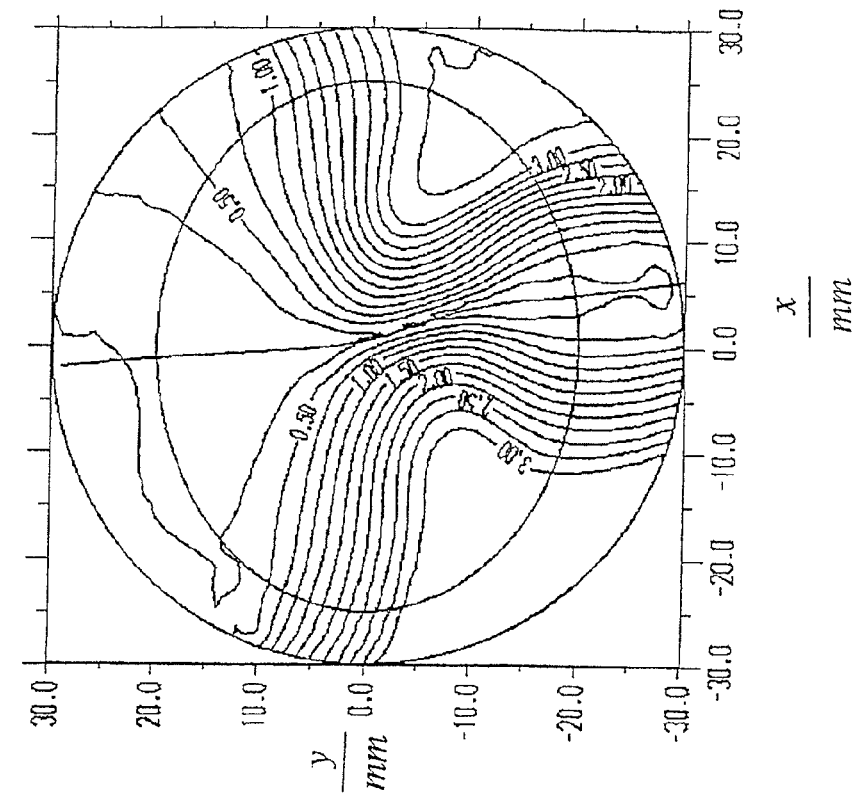
FIG. 7A illustrates exemplary isoastigmatism lines of the refraction deficit of a spectacle lens optimized without considering the direction of sight of the other eye, for an evaluation with consideration of the direction of sight of the other eye.
Figure 7B:
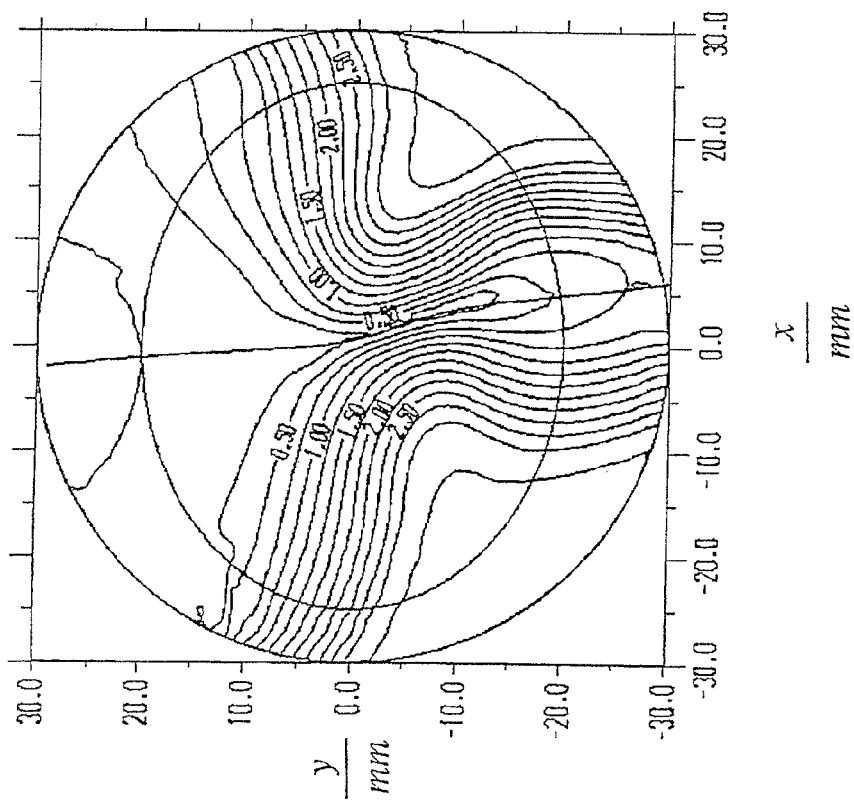
FIG. 7B illustrates exemplary isoastigmatism lines of the refraction deficit of a spectacle lens of a spectacle lens pair optimized with consideration of the direction of sight of the other eye, for an evaluation with consideration of the direction of sight of the other eye.
Figure 7C:
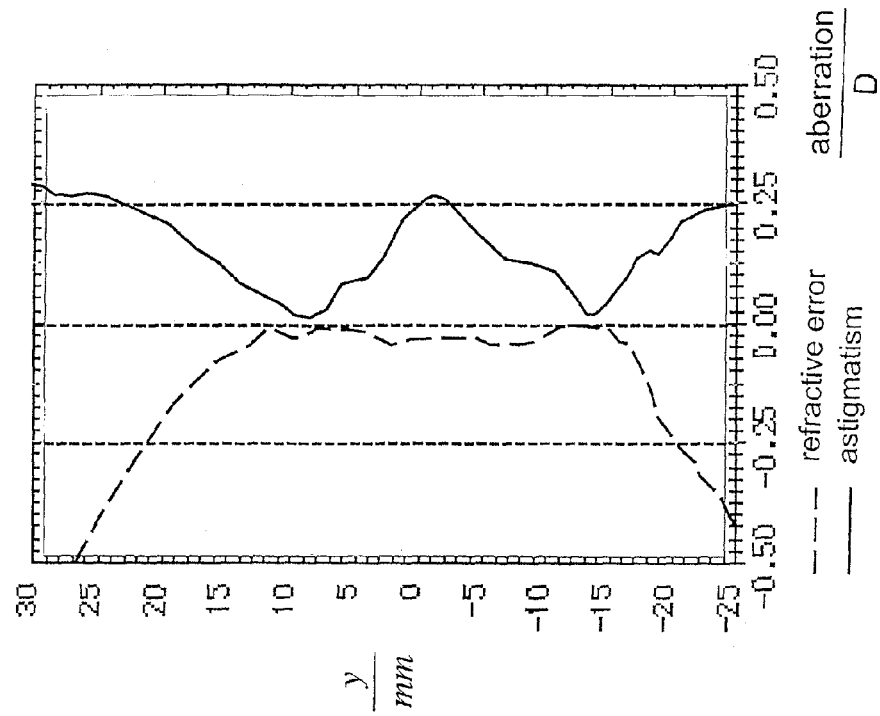
FIG. 7C illustrates an exemplary a course of the refraction deficit with respect to the refractive power (left curve) and the astigmatism (right curve) along the main line of FIG. 7A.
Figure 7D:
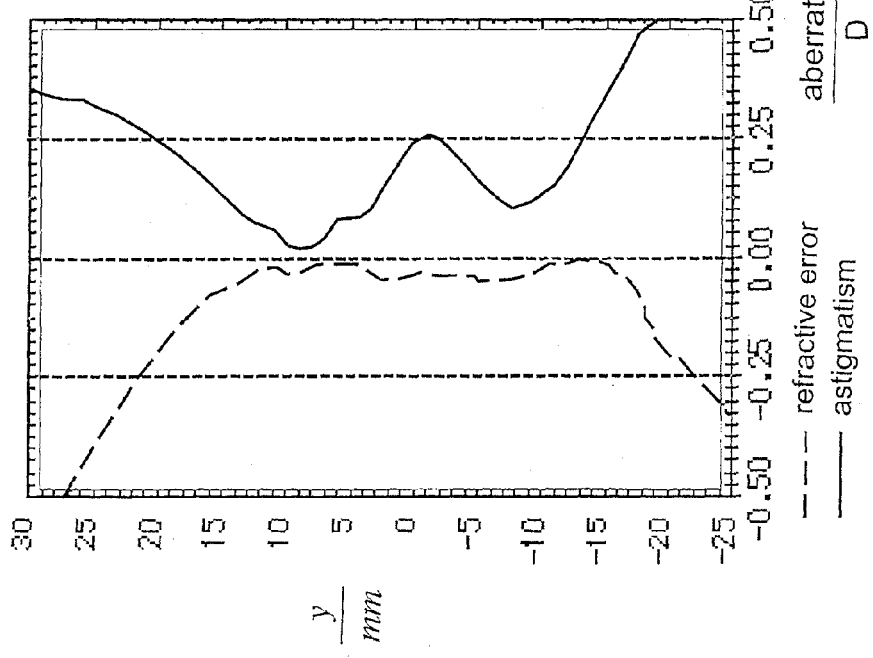
FIG. 7D illustrates an exemplary course of the refraction deficit with respect to the refractive power (left curve) and the astigmatism (right curve) along the main line of FIG. 7B.

Now, if the optimization is performed according to the model L2, a new lens is formed, which is illustrated in FIGS. 7B and 7D. For the sake of comparison, FIGS. 7A and 7C show the same graphics as FIGS. 6B and 6D for the L1-optimized lens considered with L2. It can be seen that the L2-assessed astigmatism on the main line resumes a similarly good course as the L1-assessed value of the L1-lens due to the L2 optimization.

The fact that the shown comparisons also have slight differences in the distance portion is due to the slight prismatic differences occurring in real ray paths due to the power course.

The embodiment according to L2 shown in the drawings is disclosed in the table of FIG. 8 for a lens that belongs to the prescription sph 2.0 D, which is the same on the right and on the left. The optimized back surface is shown, the front surface is spherical with a base curve of 8.5 D. The material has a refractive index of n=1.597, the lens has a center thickness of 7.16 mm. Due to the position of the prism reference point at (x,y)=(0,0) in the coordinates indicated in the table (first line or column of the part of the table each), the construction of the lens becomes clearly comprehensible.

The illustrated spectacle lens results in particular after one single primary calculation or optimization step. For a preferred optimization and production of a spectacle lens pair, this spectacle lens subsequently remains unchanged and the other spectacle lens is determined accordingly in a secondary calculation or optimization step. Alternatively, the other spectacle lens might also be determined by copying and mirroring the shown spectacle lens. In a preferred embodiment, this other spectacle lens remains unchanged in the form obtained in the secondary calculation or optimization step or by copying or mirroring, and the one spectacle lens (which has been optimized first) is optimized further in a tertiary calculation or optimization step. These calculation or optimization steps are iterated or repeated preferably until a sufficient convergence of the calculation or optimization method has been achieved, i.e. until the deviations of successive optimization results of the individual spectacle lenses are sufficiently small, in particular smaller than a predetermined threshold.

Figure 9:
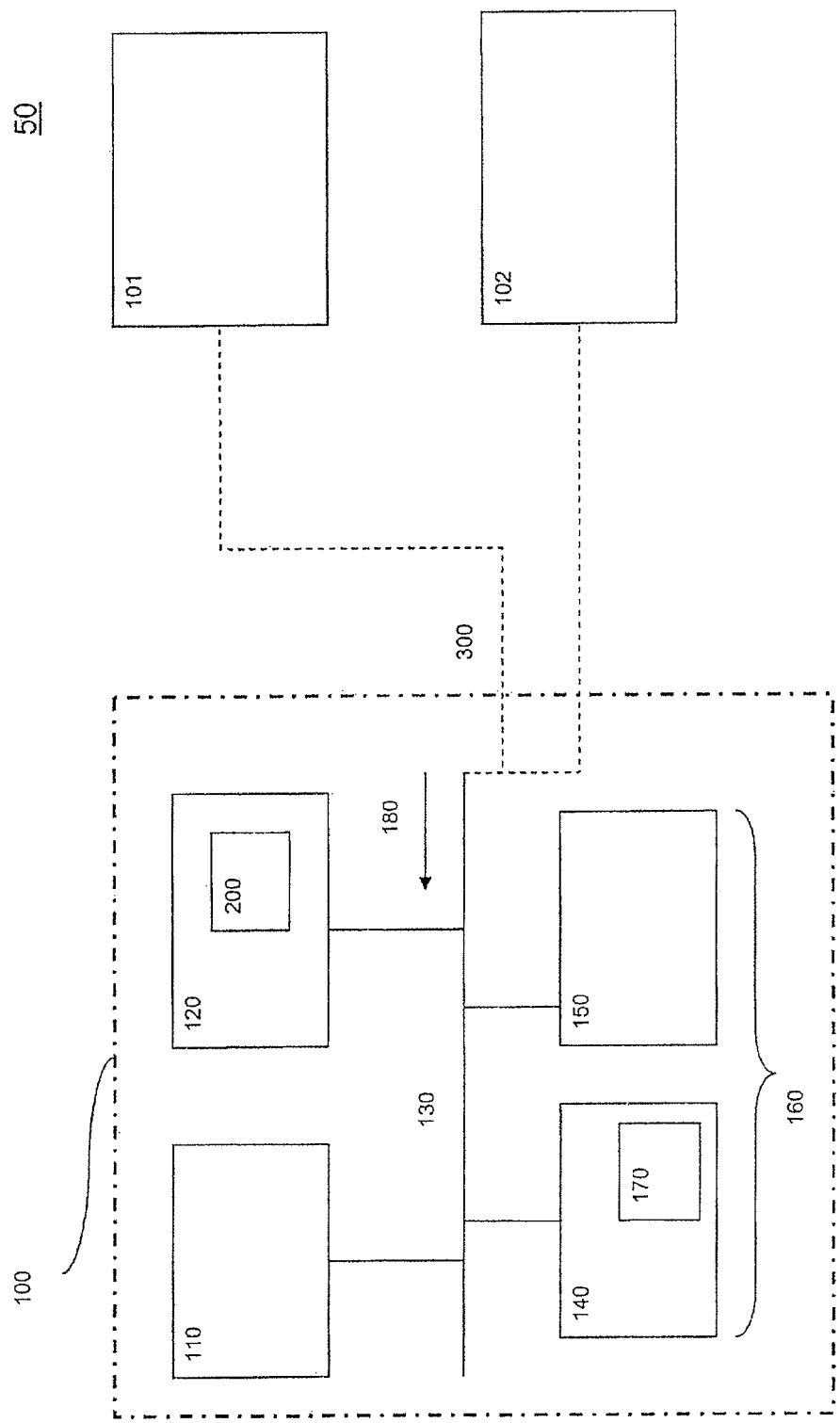
FIG. 9 illustrates a schematic representation of an apparatus for optimizing and producing a spectacle lens or a spectacle lens pair according to an exemplary embodiment.

As is schematically illustrated in FIG. 9, a computer program product (i.e. a computer program claimed in the patent category of an apparatus) 200 is further provided, which is adapted such that, when loaded and executed on a suitable computer 100 or network, it can perform a method for optimizing or producing at least one spectacle lens pair to be used in spectacles for a specific situation of wear. The computer program product 200 can be stored on a physical storage medium or program carrier 120. The computer program product can further be provided as a program signal.

A possible computer or network architecture will be described in the following with reference to FIG. 9. The processor 110 of the computer 100 is a central processor (CPU), a microcontroller (MCU), or a digital signal processor (DSP), for example. The memory 120 symbolizes elements storing data and commands either in a temporally limited or permanent fashion. Even though the memory 120 is shown as part of the computer 100 for the sake of better understanding, the storage function can be implemented elsewhere, e.g. in the processor itself (e.g. cache, register) and/or also in the network 300, for example in the computers 101/102. The memory 120 may be a Read-Only Memory (ROM), a Random-Access Memory (RAM), a programmable or non-programmable PROM, or a memory with other access options. The memory 120 can physically be implemented or stored on a computer-readable program carrier, for example on:

(a) a magnetic carrier (hard disk, floppy disk, magnetic tape);
(b) an optical carrier (CD-ROM, DVD);
(c) a semiconductor carrier (DRAM, SRAM, EPROM, EEPROM).

Optionally, the memory 120 is distributed across different media. Parts of the memory 120 can be attached in a fixed or exchangeable manner. The computer 100 uses known means, such as floppy-disk drives, for reading and writing.

The memory 120 stores support components, such as a Bios (Basic Input Output System), an operating system (OS), a program library, a compiler, an interpreter and/or a spreadsheet or word processing program. These components are not illustrated for the sake of better understanding. Support components are commercially available and can be installed or implemented on the computer 100 by experts.

The processor 110, the memory 120, the input and output devices are connected via at least one bus 130 and/or are optionally coupled via the (mono, bi, or multi-directional) network 300 (e.g. the Internet) or are in communication with each other. The bus 130 and the network 300 represent logical and/or physical connections, which transmit both commands and data signals. The signals within the computer 100 are mainly electrical signals, whereas the signals in the network are electrical, magnetic and/or optical signals or also wireless radio signals.

Network environments (such as the network 300) are common in offices, company-wide computer networks, Intranets, and on the Internet (i.e. World Wide Web). The physical distance between the computers in the network does not have any significance. The network 300 may be a wireless or wired network. Possible examples for implementations of the network 300 are: a Local Area Network (LAN), a Wireless Local Area Network (WLAN), a Wide Area Network (WAN), an ISDN network, an infrared link (IR), a radio link, such as the Universal Mobile Telecommunication System (UMTS) or a satellite link. Transmission protocols and data formats are known. Examples are: TCP/IP (Transmission Control Protocol/Internet Protocol), HTTP (Hypertext Transfer Protocol), URL (Unique Resource Locator), HTML (Hypertext Markup Language), XML (Extensible Markup Language), WML (Wireless Application Markup Language), Wireless Application Protocol (WAP), etc.

The input and output devices may be part of a user interface 160. The input device 140 is a device that provides data and instructions to be processed by the computer 100. For example, the input device 140 is a keyboard, a pointing device (mouse, trackball, cursor arrows), microphone, joystick, scanner. Even though the examples are all devices with human interaction, preferably via a graphical user interface, the device 140 can also do without human interaction, such as a wireless receiver (e.g. by a satellite or terrestrial antenna), a sensor (e.g. a thermometer), a counter (e.g. a piece counter in a factory). The input device 140 can be used for reading the storage medium or carrier 170.

The output device 150 designates a device displaying instructions and data that have already been processed. Examples are a monitor or a different display (cathode ray tube, flat screen, liquid crystal display, loudspeakers, printer, vibrating alert). Similar to the input device 140, the output device 150 preferably communicates with the user, preferably via a graphical user interface. The output device may also communicate with other computers 101, 102, etc.

The input device 140 and the output device 150 can be combined in one single device. Both devices 140, 150 can be provided selectively.

The computer program product 200 comprises program instructions and optionally data causing the processor 110, among others, to perform the method according to the exemplary embodiments thereof. In other words, the computer program 200 defines the function of the computer 100 and its interaction with the network system 300. For example, the computer program product 200 can be provided as a source code in an arbitrary programming language and/or as a binary code in a compiled form (i.e. machine-readable form). A skilled person is able to use the computer program product 200 with any of the above-explained support components (e.g. compiler, interpreter, operating system).

Even though the computer program product 200 is shown as being stored in the memory 120, the computer program product 100 may as well be stored elsewhere (e.g. on the storage medium or program carrier 170).

The storage medium 170 is exemplarily shown to be external to the computer 100. In order to transfer the computer program product 200 to the computer 100, the storage medium 170 can be inserted into the input device 140. The storage medium 170 can be implemented as an arbitrary computer-readably carrier, for example as one of the above-explained media (cf. memory 120). The program signal 180, which is preferably transferred to the computer 100 via the network 300, can also include the computer program product 200 or be a part of it.

Interfaces for coupling the individual components of the computer system 50 are also known. The interfaces are not shown for the sake of simplification. An interface can e.g. have a serial interface, a parallel interface, a gameport, a universal serial bus (USB), an internal or external modem, a graphics adapter and/or a soundcard.

It is particularly possible to transfer prescription data of the spectacle lenses preferably together with individual data of the spectacle wearer (including the data of the individual situation of wear) and/or data of the spectacle lens (refractive index, vertex depths of the front and back surfaces) to a device for producing a spectacle lens preferably by data remote transfer. Then, the optimization of the spectacle lens is preferably performed on the basis of the transmitted prescription data and individual data.

It should be understood that while the foregoing has been described in conjunction with exemplary embodiments, it is understood that the term "exemplary" is merely meant as an example, rather than the best or optimal. Accordingly, the disclosure herein is intended to cover alternatives, modifications and equivalents, which may be included within the spirit and scope of the disclosed apparatus and method.

Additionally, in the preceding detailed description, numerous specific details have been set forth in order to provide a thorough understanding of the present disclosure. However, it should be apparent to one of ordinary skill in the art that the embodiments described herein may be practiced without these specific details. In other instances, well-known methods, procedures, and components have not been described in detail so as not to unnecessarily obscure aspects of the disclosure herein.

List of Reference Numerals

S$1p$, S$2p$ first and second primary calculation or optimization steps, respectively
S$1s$, S$2s$ first and second secondary calculation or optimization steps, respectively
S$1t$, S$2t$ first and second tertiary calculation or optimization steps, respectively
S$1q$, S$2q$ first and second quarternary calculation or optimization steps, respectively
A(1), A(2) starting value for the first and second spectacle lenses, respectively
B(1), B(2) first and second primarily optimized spectacle lens, respectively
C(1), C(2) first and second secondarily optimized spectacle lens, respectively
D(1), D(2) first and second tertiarily optimized spectacle lens, respectively
E(1), E(2) first and second quarternarily optimized spectacle lens, respectively computer system
100, 101, 102 computer
110 processor
120 memory
130 bus
140 input device
150 output device
160 user interface
170 storage medium
180 program signal
200 computer program product
300 network

The invention claimed is:

1. A method for producing a first spectacle lens for a specific situation of wear for correcting at least a first astigmatic refraction of a first eye of a wearer, which in a reference direction of sight $-e_z^{(1)}$ of the first eye has a first cylinder reference axis $\alpha_0^{(1)}$, the method comprising:

determining a primary direction of sight $-e_\zeta^{(1,p)}$ of the first eye for at least one primary evaluation point $i_b^{(1,p)}$ of the first spectacle lens;

determining a primary direction of sight $-e_{\zeta,k}^{(2,p)}$ of a second eye of the wearer that corresponds to the primary direction of sight $-e_\zeta^{(1,p)}$ of the first eye in the specific situation of wear; and minimizing a first primary merit function to produce at least one surface of the first spectacle lens, wherein the first primary merit function for the at least one primary evaluation point $i_b^{(1,p)}$ of the first spectacle lens takes into account a correction of a first primary transformed astigmatic refraction by the first spectacle lens in the specific situation of wear such that the first primary transformed astigmatic refraction depends on the corresponding primary direction of sight $-e_{\zeta,k}^{(2,p)}$ of the second eye.

2. The method according to claim 1, wherein the first primary transformed astigmatic refraction has a first primary cylinder correction axis $\alpha_K^{(1,p)}$ that encloses a first primary correction torsion angle $\psi_K^{(1,p)}$ with a first primary torsion reference axis $e_L^{(1,p)}$, which is substantially perpendicular to the reference direction of sight $-e_z^{(1)}$ of the first eye and to the primary direction of sight $-e_\zeta^{(1,p)}$ of the first eye, and wherein the first primary correction torsion angle $\psi_K^{(1,p)}$ deviates from a first primary reference torsion angle $\psi_0^{(1,p)}$ between the first cylinder reference axis $\alpha_0^{(1)}$ and the first primary torsion reference axis $e_L^{(1,p)}$ by a first primary torsion correction angle $\psi_\Delta^{(1,p)}(e_{\zeta,k}^{(2,p)})$, which at least depends on the corresponding primary direction of sight $-e_{\zeta,k}^{(2,p)}$ of the second eye.

3. The method according to claim 2, wherein the first primary torsion correction angle $\psi_\Delta^{(1,p)}(e_\zeta^{(1,p)}, e_{\zeta,k}^{(2,p)})$ depends on the determined primary direction of sight $-e_\zeta^{(1,p)}$ of the first eye and on the determined corresponding primary direction of sight $-e_{\zeta,k}^{(2,p)}$ of the second eye.

4. The method according to claim 3, wherein it holds for the first primary torsion correction angle $\psi_\Delta^{(1)}$:

$$\psi_\Delta^{(1)} = \arctan\left(\frac{\tan\left(\frac{\vartheta_k^{(2,p)}}{2}\right)\cdot}{\tan\left(\frac{\varphi_k^{(2,p)}}{2}\right)}\right) - \arctan\left(\frac{\tan\left(\frac{\vartheta^{(1,p)}}{2}\right)\cdot}{\tan\left(\frac{\varphi^{(1,p)}}{2}\right)}\right).$$

5. The method according to claim 3, wherein it holds for the first primary torsion correction angle $\psi_\Delta^{(1)}$:

$$\psi_\Delta^{(1)} = 2\cdot\arctan\left(\frac{\tan\left(\frac{\vartheta^{(1,p)}+\vartheta_k^{(2,p)}}{4}\right)\cdot}{\tan\left(\frac{\varphi^{(1,p)}+\varphi_k^{(2,p)}}{4}\right)}\right) - 2\cdot\arctan\left(\frac{\tan\left(\frac{\vartheta^{(1,p)}}{2}\right)\cdot}{\tan\left(\frac{\varphi^{(1,p)}}{2}\right)}\right).$$

6. The method according to claim 1, wherein the step of determining the corresponding primary direction of sight $-e_{\zeta,k}^{(2,p)}$ of the second eye comprises determining a corresponding primary evaluation point $i_b^{(2,p)}$ of the second spectacle lens, which corresponds to the primary evaluation point $i_b^{(1,p)}$ of the first spectacle lens in the specific situation of wear, taking into account a prismatic power of at least one of the first spectacle lens and the second spectacle lens in the respective primary evaluation point in the specific situation of wear.

7. The method according to claim 6, further comprising:

detecting a second cylinder reference axis $\alpha_0^{(2)}$ of a second astigmatic refraction of the second eye in a reference direction of sight $-e_z^{(2)}$ of the second eye, wherein the first primary merit function depends on a correction of a second primary transformed astigmatic refraction by the second spectacle lens in the specific situation of wear, and wherein the second primary transformed astigmatic refraction has a second primary cylinder correction axis $\alpha_K^{(2,p)}$, which encloses a second primary correction torsion angle $\psi_K^{(2,p)}$ with a second primary torsion reference axis $e_L^{(2,p)}$, which is perpendicular to the reference direction of sight $-e_z^{(2)}$ of the second eye and to the corresponding primary direction of sight $-e_{\zeta,k}^{(2,p)}$ of the second eye, the second primary correction torsion angle $\psi_K^{(2,p)}$ deviating from a second primary reference torsion angle $\psi_0^{(2,p)}$ between the second cylinder reference axis $\alpha_0^{(2)}$ and the second primary torsion reference axis $e_L^{(2,p)}$ by a second primary torsion correction angle $\psi_\Delta^{(2,p)}(e_\zeta^{(1,p)})$, which at least depends on the primary direction of sight $-e_\zeta^{(1,p)}$ of the first eye.

8. The method according to claim 1, wherein the first spectacle lens is produced for correcting anisometropia.

9. The method according to claim 1, wherein the corresponding primary direction of sight $-e_{\zeta,k}^{(2,p)}$ of the second eye is determined for the at least one primary evaluation point $i_b^{(1,p)}$ of the first spectacle lens by ray tracing assuming orthotropia.

10. A method for producing a spectacle lens pair for a specific situation of wear for correcting a first astigmatic refraction of a first eye of a wearer and a second astigmatic refraction of a second eye of the wearer, in which a reference direction of sight $-e_z^{(1)}$ of the first eye has a first cylinder reference axis $\alpha_0^{(1)}$ and a reference direction of sight $-e_z^{(2)}$ of the second eye has a second cylinder reference axis $\alpha_0^{(2)}$, the method comprising:

determining a primary direction of sight $-e_\zeta^{(1,p)}$ of the first eye for at least one primary evaluation point $i_b^{(1,p)}$ of a first spectacle lens of the pair;

determining a primary direction of sight $-e_{\zeta,k}^{(2,p)}$ of a second eye of the wearer that corresponds to the primary direction of sight $-e_\zeta^{(1,p)}$ of the first eye in the specific situation of wear; and minimizing a first primary merit function to produce at least one surface of the first spectacle lens, wherein the first primary merit function for the at least one primary evaluation point $i_b^{(1,p)}$ of the first spectacle lens takes into account a correction of a first primary transformed astigmatic refraction by the first spectacle lens in the specific situation of wear such that the first primary transformed astigmatic refraction depends on the corresponding primary direction of sight $-e_{\zeta,k}^{(2,p)}$ of the second eye; and producing a second spectacle lens of the pair based on the first spectacle lens.

11. The method according to claim 10, wherein the step of producing the second spectacle lens comprises:

determining a secondary direction of sight $-e_\zeta^{(2,s)}$ of the second eye for at least one secondary evaluation point $i_b^{(2,s)}$ of the second spectacle lens;

determining a secondary direction of sight $-e_{\zeta,k}^{(1,s)}$ of the first eye of the wearer that corresponds to the secondary direction of sight $-e_\zeta^{(2,s)}$ of the second eye in the specific situation of wear, depending on the first spectacle lens; and minimizing a second secondary merit function to produce at least one surface of the second spectacle lens, wherein the second secondary merit function for the at least one secondary evaluation point $i_b^{(2,s)}$ of the second spectacle lens takes into account a correction of a second secondary transformed astigmatic refraction by the second spectacle lens in the specific situation of wear such that the second secondary transformed astigmatic refraction has a second secondary cylinder correction axis $\alpha_K^{(2,s)}$, which encloses a second secondary correction torsion angle $\psi_K^{(2,s)}$ with a second secondary torsion reference axis $e_L^{(2,s)}$ that is substantially perpendicular to the reference direction of sight $-e_z^{(2)}$ of the second eye and to the secondary direction of sight $-e_\zeta^{(2,s)}$ of the second eye, said second secondary correction torsion angle $\psi_K^{(2,s)}$ deviating from a second secondary reference torsion angle $\psi_0^{(2,s)}$ between the second cylinder reference axis $\alpha_0^{(2)}$ and the second secondary torsion reference axis $e_L^{(2,s)}$ by a second secondary torsion correction angle $\psi_\Delta^{(2,s)}(e_{\zeta,k}^{(1,2)})$, which at least depends on the corresponding secondary direction of sight $-e_{\zeta,k}^{(1,s)}$ of the first eye.

12. The method according to claim 10, wherein the step of producing the second spectacle lens further comprises copying at least one surface of the first spectacle lens.

13. The method according to claim 10, comprising:
minimizing a second primary merit function to produce the at least one surface of the second spectacle lens; and
producing the first spectacle lens based on the second spectacle lens produced in the step of minimizing a second primary merit function.

14. The method according to claim 13, wherein the step of minimizing a second primary merit function comprises:
determining a primary direction of sight $-e_\zeta^{(2,p)}$ of the second eye for at least one primary evaluation point $i_b^{(2,p)}$ of the second spectacle lens;
determining a primary direction of sight $-e_{\zeta,k}^{(1,p)}$ of the first eye of the wearer that corresponds to the primary direction of sight $-e_\zeta^{(2,p)}$ of the second eye in the specific situation of wear, depending on starting values for a first spectacle lens; and
minimizing the second primary merit function for at least one surface of the second spectacle lens, wherein the second primary merit function for the at least one primary evaluation point $i_b^{(2,p)}$ of the second spectacle lens takes into account a correction of a second primary transformed astigmatic refraction by the second spectacle lens in the specific situation of wear such that the second primary transformed astigmatic refraction has a second primary cylinder correction axis $\alpha_K^{(2,p)}$, which encloses a second primary correction torsion angle $\psi_K^{(2,p)}$ with a second primary torsion reference axis $e_L^{(2,p)}$, which is perpendicular to the reference direction of sight $-e_z^{(2)}$ of the second eye and to the primary direction of sight $-e_\zeta^{(2,p)}$ of the second eye, the second primary correction torsion angle $\psi_K^{(2,p)}$ deviating from a second primary reference torsion angle $\psi_0^{(2,p)}$ between the second cylinder reference axis $\alpha_0^{(2)}$ and the second primary torsion reference axis $e_L^{(2,p)}$ by a second primary torsion correction angle $\psi_\Delta^{(2,p)}(e_{\zeta,k}^{(1,p)})$, which at least depends on the corresponding primary direction of sight $-e_{\zeta,k}^{(1,p)}$ of the first eye; and
wherein the step of producing the first spectacle lens based on the second spectacle lens comprises:
determining a secondary direction of sight $-e_\zeta^{(1,s)}$ of the first eye for at least one secondary evaluation point $i_b^{(1,s)}$ of the first spectacle lens;
determining a secondary direction of sight $-e_{\zeta,k}^{(2,s)}$ of the second eye of the wearer that corresponds to the secondary direction of sight $-e_\zeta^{(1,s)}$ of the first eye in the specific situation of wear, depending on the second spectacle lens determined in the step of minimizing a second primary merit function; and
minimizing a first secondary merit function for at least one surface of the first spectacle lens, wherein the first secondary merit function for the at least one secondary evaluation point $i_b^{(1,s)}$ of the first spectacle lens takes into account a correction of a first secondary transformed astigmatic refraction by the first spectacle lens in the specific situation of wear such that the first secondary transformed astigmatic refraction has a first secondary cylinder correction axis $\alpha_K^{(1,s)}$, which encloses a first secondary correction torsion angle $\psi_K^{(1,s)}$ with a first secondary torsion reference axis $e_L^{(1,s)}$, which is perpendicular both to the reference direction of sight $-e_z^{(1)}$ of the first eye and to the secondary direction of sight $-e_\zeta^{(1,s)}$ of the first eye, the first secondary correction torsion angle $\psi_K^{(1,s)}$ deviating from a first secondary reference torsion angle $\psi_0^{(1,s)}$ between the first cylinder reference axis $\alpha_0^{(1)}$ and the first secondary torsion reference axis $e_L^{(1,s)}$ by a first secondary torsion correction angle $\psi_\Delta^{(1,s)}(e_{\zeta,k}^{(2,s)})$, which at least depends on the corresponding secondary direction of sight $-e_{\zeta,k}^{(2,s)}$ of the second eye.

15. The method according to claim 14, further comprising:
specifying at least one of a first and a second torsion correction area of the first spectacle lens or the second spectacle lens, respectively, the respective torsion correction area comprising a multitude of first or second evaluation points $i_b$ of the first spectacle lens or the second spectacle lens, respectively;
determining the first or the second direction of sight $-e_\zeta$, respectively, for each evaluation point i of the first spectacle lens or the second spectacle lens, respectively, wherein the determination of the corresponding direction of sight $-e_{\zeta,k}$ of the respective other eye is performed at least for each evaluation point $i_b$ of the first torsion correction area or the second torsion correction area, respectively,
wherein the merit function, for at least each evaluation point $i_b$ of the first torsion correction area or the second torsion correction area, respectively, takes into account a correction of a respective transformed astigmatic refraction by the respective spectacle lens in the specific situation of wear such that the respective torsion correction angle $\psi_\Delta(e_{\zeta,k})$ depends on the corresponding direction of sight $-e_{\zeta,k}$.

16. The method according to claim 15, wherein in at least on of the first and the second primary merit function for each evaluation point $i^{(1)}$ of the first spectacle lens or the second spectacle lens, respectively, not comprised by the first or the second torsion correction area, respectively, takes into account a correction of a first or a second transformed astigmatic refraction by the first or the second spectacle lens, respectively, in the specific situation of wear such that the first or the second primary correction torsion angle $\psi_K^{(p)}$, respectively, matches with the first or the second primary reference torsion angle $\psi_0^{(p)}$, respectively.

17. The method according to claim 15, wherein at least one of the first torsion correction area and the second torsion correction area of the respective spectacle lens at least partially comprises a near zone of the respective spectacle lens.

18. The method according to claim 10 further comprising providing at least one of a first and a second starting surface for the at least one surface of the first spectacle or the at least one surface of the second spectacle lens, respectively, wherein the respective starting surface is determined by minimizing a monocular merit function that does not depend on the respective other spectacle lens.

19. The method according to claim 10, wherein the step of determining the primary direction of sight $-e_\zeta^{(1,p)}$ of the first eye comprises:

determining a primary first Helmholtz angle $\vartheta_{,}^{(1,p)}$ of the first eye and a primary second Helmholtz angle $\phi^{(1,p)}$ of the first eye for the at least one first primary evaluation point $i_b^{(1,p)}$ of the first spectacle lens such that the reference direction of sight $-e_z^{(1)}$ of the first eye transitions into the primary direction of sight $-e_\zeta^{(1,p)}$ of the first eye by a combination of a first rotation of the first eye about a substantially horizontal first rotation axis $e_x^{(1)}$ of the first eye, which is substantially perpendicular to the reference direction of sight $-e_z^{(1)}$ of the first eye, by the primary first Helmholtz angle $\vartheta_{,}^{(1,p)}$ of the first eye, and of a second rotation of the first eye about a primary second rotation axis $e_{y,H}^{(1,p)}$ of the first eye by the primary second Helmholtz angle $\phi^{(1,p)}$ of the first eye, wherein the primary second rotation axis $e_{y,H}^{(1)}$ of the first eye is an axis that is rotated about the first rotation axis $e_x^{(1)}$ of the first eye by the primary first Helmholtz angle $\vartheta_{,}^{(1,p)}$ of the first eye with respect to an axis $e_y^{(1)}$, which is substantially perpendicular to the reference direction of sight $-e_z^{(1)}$ of the first eye and to the first rotating axis $e_x^{(1)}$ of the first eye, and wherein the step of determining the corresponding primary direction of sight $-e_{\zeta,k}^{(2,p)}$ of the second eye comprises determining a corresponding primary first Helmholtz angle $\vartheta_{,k}^{(2,p)}$ of the second eye and a corresponding primary second Helmholtz angle $\phi_k^{(2,p)}$ of the second eye such that the reference direction of sight $-e_z^{(2)}$ of the second eye transitions into the corresponding primary direction of sight $-e_{\zeta,k}^{(2,p)}$ of the second eye by a combination of a first rotation of the second eye about a substantially horizontal first rotation axis $e_x^{(2)}$ of the second eye, which is substantially perpendicular to the reference direction of sight $-e_z^{(2)}$ of the second eye, by the corresponding primary first Helmholtz angle $\vartheta_{,k}^{(2,p)}$ of the second eye, and of a second rotation of the second eye about a corresponding primary second rotation axis $e_{y,H,k}^{(2,p)}$ of the second eye by the corresponding primary second Helmholtz angle $\phi_k^{(2,p)}$ of the second eye, wherein the corresponding primary second rotation axis $e_{y,H,k}^{(2,p)}$ of the second eye is an axis that is rotated about the first rotation axis $e_x^{(2)}$ of the second eye by the corresponding primary first Helmholtz angle $\vartheta_{,k}^{(2,p)}$ of the second eye with respect to an axis $e_y^{(2)}$, which is substantially perpendicular to the reference direction of sight $-e_z^{(2)}$ of the second eye and to the first rotating axis $e_x^{(2)}$ of the second eye.

20. The method according to claim 10, wherein the spectacle lens pair is produced for correcting anisometropia.

21. A non-transitory computer program product including program parts, which, when loaded and executed on a computer, are configured to perform a method for producing a first spectacle lens for a specific situation of wear for correcting at least a first astigmatic refraction of a first eye of a wearer, which has a first cylinder reference axis $\alpha_0^{(1)}$ in a reference direction of sight $-e_z^{(1)}$ of the first eye, the method comprises:

determining a primary direction of sight $-e_\zeta^{(1,p)}$ of the first eye for at least one primary evaluation point $i_b^{(1,p)}$ of the first spectacle lens;

determining a primary direction of sight $-e_{\zeta,k}^{(2,p)}$ of a second eye of the wearer that corresponds to the primary direction of sight $-e_\zeta^{(1,p)}$ of the first eye in the specific situation of wear; and minimizing a first primary merit function to produce at least one surface of the first spectacle lens, wherein the first primary merit function for the at least one primary evaluation point $i_b^{(1,p)}$ of the first spectacle lens takes into account a correction of a first primary transformed astigmatic refraction by the first spectacle lens in the specific situation of wear such that the first primary transformed astigmatic refraction depends on the corresponding primary direction of sight $-e_{\zeta,k}^{(2,p)}$ of the second eye.

22. A non-transitory storage medium with a computer program stored thereon, said computer program being adapted, when loaded and executed on a computer, to perform a method for producing a first spectacle lens for a specific situation of wear for correcting at least a first astigmatic refraction of a first eye of a wearer, which has a first cylinder reference axis $\alpha_0^{(1)}$ in a reference direction of sight $-e_z^{(1)}$ of the first eye, the method comprises:

determining a primary direction of sight $-e_\zeta^{(1,p)}$ of the first eye for at least one primary evaluation point $i_b^{(1,p)}$ of the first spectacle lens;

determining a primary direction of sight $-e_{\zeta,k}^{(2,p)}$ of a second eye of the spectacle wearer that corresponds to the primary direction of sight $-e_\zeta^{(1,p)}$ of the first eye in the specific situation of wear; and minimizing a first primary merit function to produce at least one surface of the first spectacle lens, wherein the first primary merit function for the at least one primary evaluation point $i_b^{(1,p)}$ of the first spectacle lens takes into account a correction of a first primary transformed astigmatic refraction by the first spectacle lens in the specific situation of wear such that the first primary transformed astigmatic refraction depends on the corresponding primary direction of sight $-e_{\zeta,k}^{(2,p)}$ of the second eye.

23. An apparatus for producing at least a first spectacle lens, the apparatus comprises:

measuring unit configured to measure merit data of a first spectacle lens;

calculation unit for calculating a first spectacle lens for a specific situation of wear for correcting at least a first astigmatic refraction of a first eye of a wearer, which has a first cylinder reference axis $\alpha_0^{(1)}$ in a reference direction of sight $-e_z^{(1)}$ of the first eye, wherein the calculation units is configured to:

determine a primary direction of sight $-e_\zeta^{(1,p)}$ of the first eye for at least one primary evaluation point $i_b^{(1,p)}$ of the first spectacle lens;

determine a primary direction of sight $-e_{\zeta,k}^{(2,p)}$ of a second eye of the spectacle wearer that corresponds to the primary direction of sight $-e_\zeta^{(1,p)}$ of the first eye in the specific situation of wear; and minimize a first primary merit function to produce at least one surface of the first spectacle lens, wherein the first primary merit function for the at least one primary evaluation point $i_b^{(1,p)}$ of the first spectacle lens takes into account a correction of a first primary transformed astigmatic refraction by the first spectacle lens in the specific situation of wear such that the first primary transformed astigmatic refraction depends on the corresponding primary direction of sight $-e_{\zeta,k}^{(2,p)}$ of the second eye.

* * * * *